US006793923B2

(12) United States Patent
Brown et al.

(10) Patent No.: US 6,793,923 B2
(45) Date of Patent: Sep. 21, 2004

(54) VACCINES WITH ENHANCED IMMUNE RESPONSE AND METHODS FOR THEIR PREPARATION

(75) Inventors: Robert George Brown, Dartmouth (CA); William Pohajdak, Dartmouth (CA); Warwick Charles Kimmins, Halifax (CA)

(73) Assignee: Immunovaccine Technologies, Inc. (CA)

( * ) Notice: Subject to any disclaimer, the term of this patent is extended or adjusted under 35 U.S.C. 154(b) by 22 days.

(21) Appl. No.: 09/992,149

(22) Filed: Nov. 6, 2001

(65) Prior Publication Data

US 2002/0110568 A1 Aug. 15, 2002

Related U.S. Application Data

(60) Provisional application No. 60/246,075, filed on Nov. 7, 2000, and provisional application No. 60/307,159, filed on Jul. 24, 2001.

(51) Int. Cl.$^7$ .................... A61K 39/00; A61K 38/00; A61K 9/127; A01N 37/18; A01N 59/06
(52) U.S. Cl. .................... 424/184.1; 424/450; 424/455; 424/561; 424/812; 424/193.1; 424/283.1; 424/689; 424/690; 424/698; 514/2; 514/937
(58) Field of Search ............................ 424/184.1, 450, 424/455, 561, 812, 193.1, 283.1, 689, 690, 698, 559, 235.1; 514/2, 937

(56) References Cited

U.S. PATENT DOCUMENTS

| | | | | |
|---|---|---|---|---|
| 5,015,476 A | * | 5/1991 | Cochrum et al. | 424/423 |
| 5,340,588 A | * | 8/1994 | Domb | 424/450 |
| 5,422,109 A | | 6/1995 | Brancq et al. | |
| 5,637,300 A | * | 6/1997 | Dunbar et al. | 424/184.1 |
| 5,709,879 A | * | 1/1998 | Barchfeld et al. | 424/450 |
| 5,736,141 A | * | 4/1998 | Brown et al. | 424/184.1 |
| 5,820,879 A | * | 10/1998 | Fernandez et al. | 424/450 |
| 5,897,873 A | | 4/1999 | Popescu | 424/450 |
| 5,910,306 A | * | 6/1999 | Alving et al. | 424/184.1 |
| 5,919,480 A | * | 7/1999 | Kedar et al. | 424/450 |
| 5,980,898 A | * | 11/1999 | Glenn et al. | 424/184.1 |
| 6,090,406 A | | 7/2000 | Popescu et al. | 424/450 |
| 6,093,406 A | | 7/2000 | Alving et al. | 424/272.1 |
| 6,110,492 A | * | 8/2000 | Alving et al. | 424/450 |
| 6,168,804 B1 | * | 1/2001 | Samuel et al. | 424/450 |
| RE37,224 E | * | 6/2001 | Brown et al. | 424/184.1 |
| 6,309,569 B1 | * | 10/2001 | Farrar et al. | 264/4.1 |
| 6,406,719 B1 | * | 6/2002 | Farrar et al. | 424/489 |
| 6,534,064 B1 | * | 3/2003 | O'Hagan et al. | 424/205.1 |
| 6,537,966 B1 | * | 3/2003 | Duan et al. | 514/2 |
| 6,565,777 B2 | * | 5/2003 | Farrar et al. | 264/4.1 |
| 6,670,195 B1 | * | 12/2003 | Ghiso et al. | 436/513 |
| 2002/0110568 A1 | * | 8/2002 | Brown et al. | 424/204.1 |

FOREIGN PATENT DOCUMENTS

| | | | | |
|---|---|---|---|---|
| WO | | 9200081 | 1/1992 | |
| WO | | WO 93/25231 | * 12/1993 | A61K/39/00 |
| WO | | WO 00/37100 | * 6/2000 | A61K/39/00 |
| WO | | 0037100 | 6/2000 | |
| WO | | WO 03/066680 A2 | * 8/2003 | C07K/14/705 |

OTHER PUBLICATIONS

Gupta et al, Vaccine, 1993, 11/13:293–306.*
Edelman et al, Intern. Rev. Immunol., 1990, 7/1:51–66.*
Nash et al, J. Reprod. Immunol., 1985, 7:151–162.*
Brown et al, J. Reprod. Immunol., 1997, 35:53–64.*
R. Gupta et al.: Adjuvants for human vaccines—current status, problems and future prospects. Vaccine, vol. 13, No. 14, Oct. 1995, pp. 1263–1276.
A. Hilbert et al.: "Biodegradable microspheres containing influenza A vaccine: immune response in mice." Vaccine, vol. 17, No. 9–10, Mar. 1999, pp. 1065–1073.
H. Nash, et al.: Formulation of a potential antipregnancy vaccine based on the beta–subunit of human chorionic gonadotropin (beta hCG). II. Use of compounds of the muramyl dipeptide (MDP) family as adjuvants. Journal of Reproductive Immunology, vol. 7, No. 2, 1985, pp. 151–162.
D. Pye et al.: "Selction of an adjuvant for vaccination with the malaria antigen, MSA–2" Vaccine, vol. 15, No. 9, Jun. 1987, pp. 1017–1023.
Ivanova, et al., 1995. "Contraceptive potential of porcine zona pellucida in cats." *Theriogenology*. 43:969–981.
Sacco et al., 1989. "Effect of varying dosage and adjuvants on antibody response in squirrel monkeys (*Saimiri sciureus*) immunized with the porcine zona pellucida Mr=55,000 glycoprotein (ZP3)." *Am. J. Reprod. Immunol.* 21:1–8.
Bagavant et al., 1994. "Antifertility effects of porcine zona pellucida–3 immunization using permissible adjuvants in female bonnet monkeys (*Macaca radiata*): reversibility, effect on follicular development and hormonal profiles." *J. Reprod. Fertil.* 102:17–25.
Muderhwa et al. ("Oil–in–water liposomal emulsions: Characterization and potential use in vaccine delivery", (Dec., 1999) *J Pharm Sci.* 88(12):1332–9.
Gregoriadis G.(1990) Immunological adjuvants: A role for liposomes, Immunol. Today 11:89–97.
Frezard, F. (1999) Liposomes: From biophysics to the design of peptide vaccines. Braz. J. Med. Bio. Res 32:181–189.

(List continued on next page.)

*Primary Examiner*—Nita Minnifield
(74) *Attorney, Agent, or Firm*—Welsh & Katz, Ltd.

(57) ABSTRACT

The present invention is concerned with vaccines and their preparation. An effective long-term immune response, especially in mammals, can be produced using a vaccine comprising an antigen encapsulated in liposomes, a suitable adjuvant and a carrier comprising a continuous phase of a hydrophobic substance. The vaccine is particularly effective in eliciting the production of antibodies that recognize epitopes of native proteins.

14 Claims, 1 Drawing Sheet

OTHER PUBLICATIONS

Figure 1:
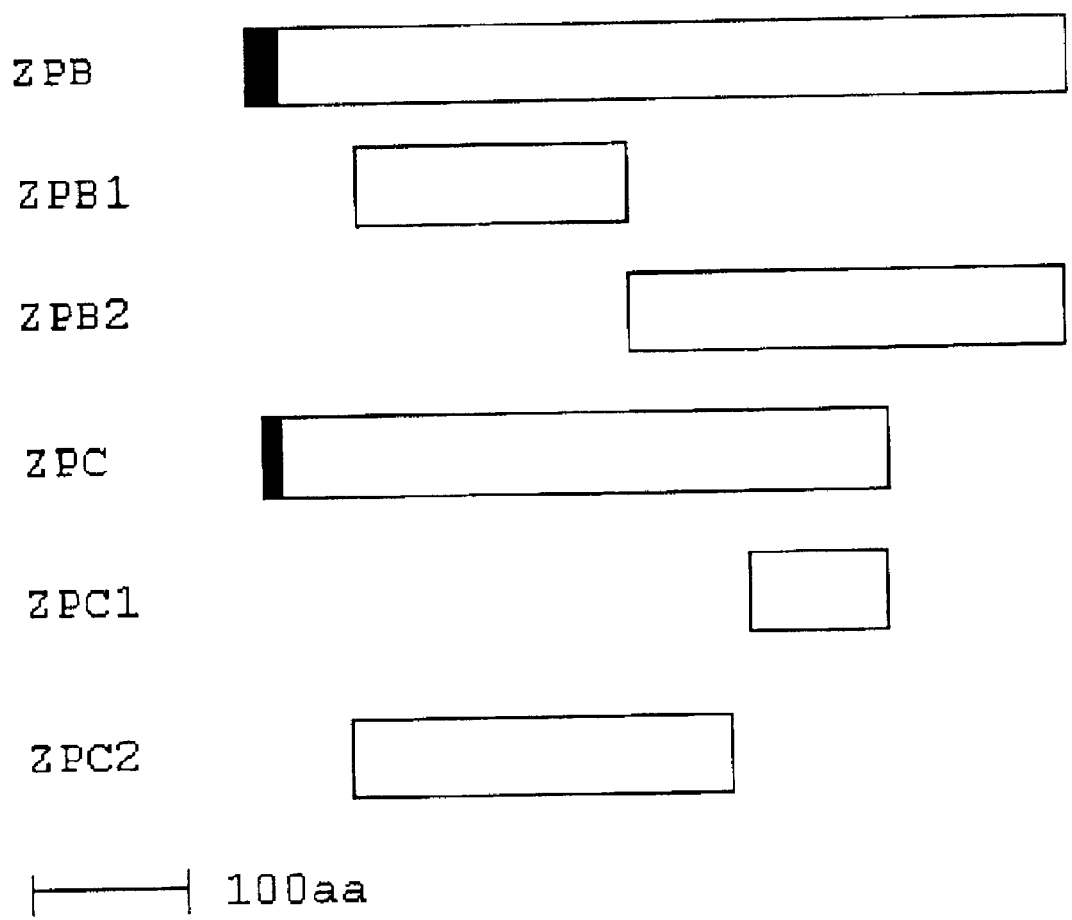

Brown, R.G., W.D.Bowen, J.D.Eddington, W.C.Kimmins, M.Mezei, J.L.Parsons, B.Pohajdak. (1997) Temporal trends in antibody production in captive grey seals, harp and hooded seals to a single administration immunocontraceptive vaccine. *J. Reproductive Immunology* 35:53–64.

Jentoft, N. and D.G.Dearborn. 1979. Labelling of proteins by reductive methylation using sodium cyanoborohydride. *J. Biol. Chem.* 254:4359–4365.

Willard et al., Pregnancy detection and the effects of age, body weight, and previous reproductive performance on pregnancy status and weaning rates of farmed fallow deer (*Dama dama*). *J. Animal Science*. 77:32–38 (1999).

Teuten et al., 1993, *Biochem. J.* 290:313–319.

Torrens et al., 1999, *Immunology Letters* 70:213–218.

Parrado et al., 1996, *Protein Sci* 5:693–704.

Connejero–Lara et al., 1996, *Protein Sci* 5:2583–2591.

Muttilainen, et al., 1995, *Microbial Pathogenesis* 18:423–436.

The National Wildlife Research Center web site. www.a-phis.usda.gov/ws/nwrc/pzp.htm "Porcine Zona Pellucida Immunocontraception in Mammals".

* cited by examiner

VACCINES WITH ENHANCED IMMUNE RESPONSE AND METHODS FOR THEIR PREPARATION

RELATED APPLICATIONS

This application claims the benefit of U.S. Provisional Applications U.S. Serial No. 60/246,075 filed Nov. 7, 2000 and U.S. Serial No. 60/307,159 filed Jul. 24, 2001, the disclosures of which are hereby incorporated by reference in their entirety.

FIELD OF THE INVENTION

The present invention relates to the field of immunology, in particular, to vaccines and their preparation.

BACKGROUND OF THE INVENTION

Generally, vaccines use low doses of a specific antigen to build up resistance in a host to the effects of larger doses of the antigen or similar antigenic compounds. Antigens used in vaccines are usually parts of whole organisms or denatured toxins (toxoids) that induce the production of antibodies. Unfortunately, only some of the antibodies produced bind to the target organism or toxin because, in most cases, the antigen used in the vaccine differs structurally from the target. The limited availability of useful antigens has posed limitations to vaccine development in the past. Advances in genetic engineering have made the production of antigens by recombinant means possible. However, use of antigens produced by recombinant means often results in poor production of antibodies with poor affinity for the target native antigen for reasons given above. The effect of immunization can be enhanced when more antibodies with high affinity for their target are produced. There is a need in the art to develop vaccines that produce an enhanced immune response without increasing the amount of antigen used in the vaccine. Particularly, there is a need for single administration vaccines that eliminate or reduce the need for booster immunizations.

Many immunization strategies would benefit from such development. Vaccines that use antigens derived from mammalian, viral, bacterial, fungal or yeast sources have many uses. For example, antigens from viral, bacterial, fungal or yeast sources are useful in the prevention of disease. Antigens from mammals may be used in cancer therapy or immunocontraception. Immunocontraceptive vaccines use mammalian derived antigens that result in transient infertility or sterility of a host, particularly a mammalian host, by favouring the production of antibodies with affinity for the oocyte surface. Immunocontraceptive vaccines find use in the control of wild animal populations, including populations of feral domestic animals such as cats.

In particular, feral cat populations have been difficult to control and threaten many birds and small animals. Stray feral cats also act as vectors for human and animal diseases. Various methods including hunting, trapping and poisoning have been used in an effort to control stray cat populations but these methods have met with limited success and with public opposition. Surgical sterilization of feral cats has been increasingly used as a humane tool to lower feral cat populations during the last two decades. Acceptance of this procedure is widespread; however, disadvantages include cost, changes in behaviour and risk of infection and mortality. Despite the success of large-scale surgical sterilization, such programs are not financially or logistically feasible in many locations since capture of animals is time-consuming, difficult and stressful for the animal. Immunocontraception offers an alternate procedure with lower costs and ease of administration. However, long-term immunocontraception generally requires booster vaccinations, making it impractical for the control of wild and free-roaming species.

Vaccines generally comprise an antigen, which elicits the immune response in the host, and a variety of carriers, excipients and adjuvants useful for administering the antigen to the host.

Liposomes, which encapsulate the antigen, have increasingly been used in vaccine delivery. It has been shown that liposome delivery of denatured antigens favours the production of antibodies that recognize native epitopes (Muttilainen, S., I. Idanpaan-Heikkila, E. Wahlstrom, M. Nurminen, P. H. Makela and M. Sarvas. 1995. "The *Neisseria meningitidis* outer membrane protein P1 produced in *Bacillus subtilis* and reconstituted into phospholipid vesicles elicits antibodies to native P1 epitopes." *Microbial Pathogen.* 18:423–436). While liposomes are useful vaccine delivery vehicles, their use alone has not provided an effective single dose vaccine, particularly with respect to immunocontraceptive vaccines.

Most immunocontraceptive vaccines use Freund's Complete Adjuvant (FCA) followed by Freund's Incomplete Adjuvant (FIA) in multiple injections to aid production of sufficient antibodies to have an immunocontraceptive effect (see Ivanova, et al., 1995. "Contraceptive potential of porcine zona pellucida in cats." *Theriogenology.* 43:969–981 and Sacco et al., 1989. "Effect of varying dosage and adjuvants on antibody response in squirrel monkeys (*Saimiri sciureus*) immunized with the porcine zona pellucida Mr=55,000 glycoprotein (ZP3)." Am. J. Reprod. Immunol. 21:1–8). Other adjuvants such as Ribi™ and TiterMax™ have been used by some investigators. Alum (aluminum phosphate and/or hydroxide) has a long history of use as an adjuvant. Alum is the only adjuvant recognized as safe by the Food and Drug Administration. Many immunocontraceptive vaccines that use alum require a primary injection and several booster injections to produce sufficient antibodies for an immunocontraceptive effect (see Bagavant et al., 1994. "Antifertility effects of porcine zona pellucida-3 immunization using permissible adjuvants in female bonnet monkeys (*Macaca radiata*): reversibility, effect on follicular development and hormonal profiles." *J. Reprod. Fertil.* 102:17–25). Some studies have shown that alum is not a suitable adjuvant for zona pellucida immunocontraceptive vaccines (see Sacco et al., 1989. *Am. J. Reprod. Immunol.* 21:1–8 and Bagavant et al., 1994. *J. Reprod. Fertil.* 102:17–25).

Prior art has generally relied on the use of an aqueous medium or oil-in-water emulsions as carriers. For example, Muttilainen et al. (*Microbial Pathogen.* 18:423–436 (1995) use an aqueous medium in combination with liposomal delivery to elicit an immune response. Popescu (U.S. Pat. No. 5,897,873 issued Apr. 27, 1999 and U.S. Pat. No. 6,090,406 issued Jul. 18, 2000), Alving (U.S. Pat. No. 6,093,406 issued Jul. 25, 2000 and U.S. Pat. No. 6,110,492 issued Aug. 29, 2000) and Muderhwa et al. ("Oil-in-water liposomal emulsions: Characterization and potential use in vaccine delivery", (December, 1999) *J Pharm Sci.* 88(12) :1332–9) also use liposomal systems together with an oil-in-water carrier as the delivery system in a vaccine. Popescu uses alum with liposomes consisting of cholesterol esterified with succinate or other organic acids. U.S. Pat. No. 6,093, 406 teaches the use of alum and liposomes comprising Lipid A or non-pyrogenic Lipid A in an oil-in-water emulsion to deliver a vaccine based on malarial antigens. U.S. Pat. No. 6,110,492 and Muderhwa teach the use of liposomes comprising Lipid A or non-pyrogenic Lipid A in an oil-in-water emulsion to deliver prostrate specific antigens.

Commonly owned U.S. Pat. No. 5,736,141, issued on Apr. 7, 1998, teaches a single dose immunocontraceptive vaccine for seals derived from zona pellucida antigens. While the results achieved with this vaccine are good, there is still a need for a single-dose, long lasting immunocontraceptive vaccine effective in a variety of species using adjuvants approved by the Food and Drug Administration.

There also remains a need for long lasting immunovaccines in general which are effective using a variety of antigens in a variety of species using adjuvants approved by the Food and Drug Administration.

SUMMARY OF THE INVENTION

In accordance with the invention, there is provided a composition for use as a vaccine, comprising:
(a) a carrier comprising a continuous phase of a hydrophobic substance;
(b) liposomes;
(c) an antigen; and,
(d) a suitable adjuvant.

There is further provided a method for potentiating an immune response in an animal, which method comprises administering to the animal an effective amount of a vaccine composition comprising:
(a) a carrier comprising a continuous phase of a hydrophobic substance;
(b) liposomes;
(c) an antigen; and,
(d) a suitable adjuvant.

Still further there is provided a method of preparing a vaccine composition comprising the steps of:
(a) encapsulating an antigen or an antigen/adjuvant complex in liposomes to form liposome-encapsulated antigen;
(b) mixing the liposome-encapsulated antigen with a carrier comprising a continuous phase of a hydrophobic substance; and,
(c) adding a suitable adjuvant if an antigen/adjuvant complex is not used in part (a).

Unexpectedly and uniquely, it has now been found that using a continuous phase of a hydrophobic substance as the carrier in a vaccine composition of the present invention enhances the immune response. The enhanced response is characterized by long-lived high antibody titres following a single vaccine administration resulting in enhanced duration of the immune response. This is particularly true for vaccines that also comprise liposome-encapsulated antigen and an adjuvant (or mixture of antigen/adjuvant). Vaccine compositions of the present invention are generally effective as a single dose providing a long-term immune response in a variety of species, typically not requiring boosters.

DETAILED DESCRIPTION OF THE INVENTION

While not being held to any particular theory of action, it is thought that, when a vaccine composition of the present invention is used, IgG antibody production occurs in two phases and the antibodies produced in each phase differ in their epitope recognition. The antibodies produced in the second phase of IgG production have more affinity for native protein antigens, thus making the vaccine more effective. Use of conventional vaccines with a primary and booster injection produces antibodies having different binding specificity for an antigen than use of a vaccine composition of the present invention.

The carrier comprises a continuous phase of a hydrophobic substance, preferably a liquid hydrophobic substance. The continuous phase may be an essentially pure hydrophobic substance, a mixture of hydrophobic substances, an emulsion of water-in-a hydrophobic substance or an emulsion of water-in-a mixture of hydrophobic substances.

Hydrophobic substances that are useful in the present invention are those that are pharmaceutically and/or immunologically acceptable. Ideally, the hydrophobic substance is one that has been approved for use by health regulatory agencies such as the U.S. Food and Drug Administration. The carrier is preferably a liquid but certain hydrophobic substances that are not liquids at atmospheric temperature may be liquified, for example by warming, and are also useful in this invention.

Oil or water-in-oil emulsions are particularly suitable carriers for use in the present invention. Oils should be pharmaceutically and/or immunologically acceptable. Preferred examples of oils are mineral oil (especially light or low viscosity mineral oil), vegetable oil (e.g. corn or canola oil), nut oil (e.g. peanut oil) and squalene. A low viscosity mineral oil is most preferred. Animal fats and artificial hydrophobic polymeric materials, particularly those that are liquid at atmospheric temperature or that can be liquified relatively easily, may also be used.

The amount of hydrophobic substance used is not critical but is typically from about 0.1 ml per dose to about 1.5 ml per dose, depending on the size of the animal and the amount of antigen being used. For small animals, the amount of hydrophobic substance is preferably from about 0.20 ml to about 1.0 ml per dose, while for large animals, the amount is preferably from about 0.45 ml to about 1.5 ml per dose. Typically, 0.25 ml per dose is used for small animals while 0.5 ml per dose is used for large animals.

Suitable antigens are any chemicals that are capable of producing an immune response in a host organism. Preferably, the antigen is a suitable native, non-native, recombinant or denatured protein or peptide, or a fragment thereof, that is capable of producing the desired immune response in a host organism. Host organisms are preferably animals (including mammals), more preferably cats, rabbits, horses and/or deer. The antigen can be of a viral, bacterial, protozoal or mammalian origin. Antigens are generally known to be any chemicals (typically proteins or other peptides) that are capable of eliciting an immune response in a host organism. More particularly, when an antigen is introduced into a host organism, it binds to an antibody on B cells causing the host to produce more of the antibody. For a general discussion of antigens and the immune response, see Kuby, J., *Immunology* $3^{rd}$ Ed. W.H. Freeman & C. NY (1997), the disclosure of which is hereby incorporated by reference.

Antigens that elicit an immune response related to cancer, contraception and other biological conditions or effects may be used in the preparation of immunovaccines. Some typical, non-limiting examples of antigens that may be used are alcohol dehydrogenase (ADH), streptokinase, hepatitis B surface antigen and zona pellucida (ZP) glycoproteins.

When the desired immune response is contraception in mammals, the target epitopes are found on mammalian oocytes. Zona pellucida (ZP) glycoproteins or recombinant proteins or peptide fragments derived therefrom may be used in this case. In particular, heat extracted solubilized isolated zona pellucida glycoproteins (SIZP) may be used as the antigen in an immunocontraceptive vaccine. More particularly, soluble intact porcine zona pellucida may be used.

The amount of antigen used in a dose of the vaccine composition can vary depending on the type of antigen and the size of the host. One skilled in the art will be able to determine, without undue experimentation, the effective amount of antigen to use in a particular application.

In the case of SIZP, the amount typically used falls in the range from about 15 µg to about 2 mg per dose. Preferably, the range is from about 20 µg to about 2 mg per dose, more preferably from about 20 µg to about 200 µg, and even more preferably from about 40 µg to about 120 µg. Typically, the amount for a small animal is about 50 µg per dose while for a large animal it is about 100 µg per dose.

In compositions of the present invention, antigens produce enhanced levels of host antibodies that bind to native epitopes of the target protein. This is the case even though the antigen may be a non-native, recombinant or denatured protein or peptide, or a fragment thereof. While not wishing to be held to any particular theory, this may be due to the antigen being held in a native-like three-dimensional conformation in the liposomes.

Liposomes are completely closed lipid bilayer membranes containing an entrapped aqueous volume. Liposomes may be unilamellar vesicles (possessing a single bilayer membrane) or multilamellar vesicles (onion-like structures characterized by multimembrane bilayers, each separated from the next by an aqueous layer. A general discussion of liposomes can be found in Gregoriadis G. (1990) Immunological adjuvants: A role for liposomes, Immunol. Today 11:89–97 and Frezard, F. (1999) Liposomes: From biophysics to the design of peptide vaccines. Braz. J. Med. Bio. Res 32:181–189, the disclosures of which are hereby incorporated by reference.

Although any liposomes may be used in this invention, including liposomes made from archaebacterial lipids, particularly useful liposomes use phospholipids and unesterified cholesterol in the liposome formulation. The cholesterol is used to stabilize the liposomes and any other compound that stabilizes liposomes may replace the cholesterol. Other liposome stabilizing compounds are known to those skilled in the art. The use of the particularly preferred liposomes may result in limiting the electrostatic association between the antigen and the liposomes. Consequently, most of the antigen may be sequestered in the interior of the liposomes.

Phospholipids that are preferably used in the preparation of liposomes are those with at least one head group selected from the group consisting of phosphoglycerol, phosphoethanolamine, phosphoserine, phosphocholine and phosphoinositol. More preferred are liposomes that comprise lipids in phospholipon 90 G.

The amount of lipid used to form liposomes depends on the antigen being used but is typically in a range from about 0.05 gram to about 0.5 gram per dose of vaccine. Preferably, the amount is about 0.1 gram per dose. When unesterified cholesterol is also used in liposome formulation, the cholesterol is used in an amount equivalent to about 10% of the amount of lipid. The preferred amount of cholesterol is about 0.01 gram per dose of vaccine. If a compound other than cholesterol is used to stabilize the liposomes, one skilled in the art can readily determine the amount needed in the formulation.

In a more preferred aspect, the vaccine compositions of the present invention are essentially free from Lipid A, including non-pyrogenic Lipid A. For the purposes of this specification, when the term Lipid A is used, it is understood to encompass non-pyrogenic Lipid A as well. Lipid A is often found in liposomal formulations of the prior art. Lipid A has many undesirable side-effects which may be overcome using non-pyrogenic Lipid A, but even then, Lipid A has many pharmaceutical reactions other than the pyrogenic one and may still cause many adverse reactions. It is therefore desirable to exclude Lipid A from the compositions of this invention.

Suitable adjuvants are alum, other compounds of aluminum, Bacillus of Calmette and Guerin (BCG), TiterMax™, Ribi™, Freund's Complete Adjuvant (FCA) and AdjuVac™, a new adjuvant disclosed by the United States Department of Agriculture's (USDA) National Wildlife Research Center on their web site and described by Fagerstone, K. A. et al. (2002) Wildlife Contraception. The Wildlife Society Technical Review 02-2. 29 p. (in press). Alum, other compounds of aluminum, TiterMax™ and the new USDA adjuvant are preferred. Enhanced immune response is found even when the adjuvant is alum, which is surprising in view of the prior art (Sacco et al. 1989. Am. J. Reprod. Immunol., 21:1–8). Alum is particularly preferred as the adjuvant.

Alum is generally considered to be any salt of aluminum, in particular, the salts of inorganic acids. Hydroxide and phosphate salts are particularly useful as adjuvants. A suitable alum adjuvant is sold under the trade name, ImjectAlum™ (Pierce Chemical Company) that consists of an aqueous solution of aluminum hydroxide (45 mg/ml) and magnesium hydroxide (40 mg/ml) plus inactive stabilizers. Alum is a particularly advantageous adjuvant since it already has regulatory approval and it is widely accepted in the art.

The amount of adjuvant used depends on the amount of antigen and on the type of adjuvant. One skilled in the art can readily determine the amount of adjuvant needed in a particular application. For immunocontraception, a suitable quantity of ImjectAlum™ for a rabbit is 0.1 ml/dose of vaccine, whereas, a suitable quantity of ImjectAlum™ for a horse is 0.5 ml/dose.

The vaccine composition is generally formulated by: encapsulating an antigen or an antigen/adjuvant complex in liposomes to form liposome-encapsulated antigen and mixing the liposome-encapsulated antigen with a carrier comprising a continuous phase of a hydrophobic substance. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. Typically, when an adjuvant like alum is used, the adjuvant and the antigen are mixed first to form an antigen/adjuvant complex followed by encapsulation of the antigen/adjuvant complex with liposomes. The resulting liposome-encapsulated antigen is then mixed with the carrier. (It should be noted that the term "liposome-encapsulated antigen" may refer to encapsulation of the antigen alone or to the encapsulation of the antigen/adjuvant complex depending on the context.) This promotes intimate contact between the adjuvant and the antigen and may, at least in part, account for the surprisingly good immune response when alum is used as the adjuvant. When another is used, the antigen may be first encapsulated in liposomes and the resulting liposome-encapsulated antigen is then mixed into the adjuvant in a hydrophobic substance.

In formulating a vaccine composition that is substantially free of water, antigen or antigen/adjuvant complex is encapsulated with liposomes and mixed with a hydrophobic substance. In formulating a vaccine in an emulsion of water-in-a hydrophobic substance, the antigen or antigen/adjuvant complex is encapsulated with liposomes in an aqueous medium followed by the mixing of the aqueous medium with a hydrophobic substance. In the case of the emulsion, to maintain the hydrophobic substance in the continuous phase, the aqueous medium containing the liposomes may be added in aliquots with mixing to the hydrophobic substance.

In all methods of formulation, the liposome-encapsulated antigen may be freeze-dried before being mixed with the hydrophobic substance or with the aqueous medium as the case may be. In some instances, an antigen/adjuvant complex may be encapsulated by liposomes followed by freeze-drying. In other instances, the antigen may be encapsulated by liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant. Freeze-drying may promote better interaction between the adjuvant and the antigen resulting in a more efficacious vaccine.

Formulation of the liposome-encapsulated antigen into a hydrophobic substance may also involve the use of an emulsifier to promote more even distribution of the liposomes in the hydrophobic substance. Typical emulsifiers are well-known in the art and include mannide oleate (Arlacel™ A), lecithin, Tween™ 80, Spans™ 20,80, 83 and 85. Mannide oleate is a preferred emulsifier. The emulsifier is used in an amount effective to promote even distribution of the liposomes. Typically, the volume ratio (v/v) of hydrophobic substance to emulsifier is in the range of about 5:1 to about 15:1 with a ratio of about 10:1 being preferred.

Administration of the vaccine composition can be done by any convenient method and will depend on the antigen being used. Vaccine compositions may be administered parenterally (including intramuscularly, sub-cutaneously) or rectally. Parenteral administration is preferred.

For parenteral application, particularly convenient unit dosage forms are ampoules. Techniques that deliver the vaccine by injection and by remote delivery using darts, spring loaded syringes with jab sticks, air/carbon dioxide powered rifles, Wester gun and/or Ballistive™ biobullets and retain the biological activity are particularly preferred.

The amount of vaccine composition administered to a host may depend on the amount of antigen used in a dose and on the effective amount of antigen required for a particular application. In the case of SIZP, the size of each dose administered to an animal is typically from about 0.25 ml to about 2.0 ml depending on the size of the animal. For smaller animals (for example, cats, rabbits, etc.) the size of the dose is typically about 0.5 ml while for larger animals (for example, horses, fallow-deer, white-tail deer, etc.) the size of the dose is typically about 1.0 ml. Typically, even when the amount of SIZP is varied, the dose size is kept fairly constant.

BRIEF DESCRIPTION OF THE DRAWINGS

The invention will now be described by way of non-limiting examples having regard to the appended drawing in which:

FIG. 1 is a diagram showing the position of recombinant ZPB1 and ZPB2; ZPC1 and ZPC2 of ZPB and ZPC proteins of porcine zona pellucida that were generated in the pRSET vectors.

EXAMPLES

Example 1

Preparation of the Vaccine Composition

The vaccine composition can be formulated to be water-free or to contain various quantities of water (by using an aqueous medium, for example, saline, phosphate buffered saline (PBS) or pyrogen-free water) while maintaining a continuous oil phase. Procedure 1 described below applies to the water-free formulation of the vaccine composition. Procedure 2 described below applies to the water containing formulation of the vaccine composition, that is, the water-in-oil emulsion. The two procedures can also vary depending on the adjuvant being used. As examples, method A applies to formulations of the vaccine composition containing alum and method B applies to formulations containing Freund's Complete Adjuvant (FCA). Other adjuvants may be accommodated by adapting either method A or method B. The procedures described below incorporate porcine soluble intact zona pellucida (SIZP) as antigen, other antigens can replace SIZP in the formulation. For example, alcohol dehydrogenase (ADH), streptokinase or hepatitis B surface antigen can also be used as the antigen.

Procedure 1: Water-Free Formulation.

Method A. Alum Adjuvant.

SIZP is prepared as previously described (Brown, R. G., W. D. Bowen, J. D. Eddington, W. C. Kimmins, M. Mezei, J. L. Parsons, B. Pohajdak. (1997) Temporal trends in antibody production in captive grey seals, harp and hooded seals to a single administration immunocontraceptive vaccine. *J. Reproductive Immunology* 35:53–64). The quantity of SIZP needed for the number of doses of the vaccine being prepared is weighed (the usual quantity of SIZP used for immunization is 50 μg for small animals and 100 μg for large animals). The SIZP is dissolved in pyrogen-free distilled water to give a final concentration of 2 mg/ml. An equal volume of ImjectAlum™ (an alum product from Pierce Chemical Co., catalogue # 77161) is added and the suspension is mixed, then freeze-dried.

To form liposomes, phospholipon 90 G (or other lipids selected from phosphoglycerol, phosphoethanolamine, phosphoserine, phosphocholine, phosphoinositol, archaebacterial lipids, without limitation, that form a closed lipid bilayer containing an entrapped antigen) is weighed (0.1 g/dose of the vaccine composition). The phospholipon 90 G is mixed with cholesterol (0.01 g/dose of vaccine composition) and the mixture is dissolved in chloroform:methanol (1/1;v/v; 1.5 ml/dose of the vaccine composition). Cholesterol can be replaced with other compounds that stabilize liposomes at concentrations determined by those skilled in the art. Washed glass beads (approximately 3 mm in diameter; 15 ml for 10 doses of the vaccine) are added and the mixture is evaporated under reduced pressure using a rotary evaporator until free of chloroform:methanol. To ensure removal of all chloroform:methanol, the mixture is placed in a dessicator under reduced pressure overnight at room temperature.

The freeze-dried SIZP/alum complex is suspended in pyrogen-free distilled water (5 ml/mg SIZP) and the suspension added to the flask containing the mixture of phospholipon 90 G/cholesterol coating the flask and glass beads. The contents of the flask are allowed to stand without agitation for 30 minutes. After 30 minutes, the flask is placed in a water bath at 35–40° C. and stirred gently with a spatula to form the liposomes. A microscope is used to evaluate liposome formation and stirring is continued with increased shaking until the mixture contains predominately multilamellar liposomes recognized by those skilled in the art. The liposomes are freeze-dried and the resulting freeze-dried liposomes are suspended in low viscosity mineral oil (0.25 ml oil/dose for small animals and 0.5 ml oil/dose for large animals) containing mannide oleate as an emulsifier (10:1:oil:emulsifier:v/v). Since liposomes are suspended in oil and are not in solution, it is necessary to determine if the procedures used result in an even distribution of SIZP in each dose. To determine if freeze-dried liposomes containing SIZP are equally distributed in oil, SIZP is labelled with $^{14}$C by reductive methylation (Jentoft, N. and D. G. Dearborn. 1979. Labelling of proteins by reductive methylation using sodium cyanoborohydride. *J. Biol. Chem.* 254:4359–4365, the disclosure of which is hereby incorporated by reference) and the radioactive SIZP used to prepare two preparations of the vaccine. Individual doses of the vaccine are prepared and radioactivity in each dose determined, thereby determining the content of SIZP in each dose of the vaccine (Table 1). The distribution of SIZP in each dose of the vaccine is highly reproducible (standard deviation, SD, was less than +/−10%).

TABLE 1

Distribution of $^{14}$C-labelled SIZP in doses of the vaccine from two preparations

| Sample No. | Preparation 1 µg SIZP/dose | Preparation 2 µg SIZP/dose |
| --- | --- | --- |
| 1 | 68 | 55 |
| 2 | 66 | 53 |
| 3 | 57 | 53 |
| 4 | 65 | 62 |
| 5 | 56 | 59 |
| 6 | 51 | 57 |
| 7 | 62 | 58 |
| 8 | 55 | 60 |
| 9 | 69 | 51 |
| 10 | 54 | 59 |
| 11 | 52 | 57 |
| 12 | 61 | 61 |
| 13 | 64 | 61 |
| 14 | 61 | 60 |
| 15 | — | 56 |
| Average | 60 | 57 |
| Standard Deviation | 5.9 | 3.2 |

Method B. FCA Adjuvant.

Preparation of the vaccine composition to contain FCA as adjuvant in place of alum, is similar to method A, except SIZP by itself, rather than as a SIZP/alum complex, is encapsulated in liposomes as described above. The liposomes containing SIZP are freeze-dried, and the freeze-dried liposomes are added to FCA in aliquots with mixing to promote an equal distribution of liposomes in the oil. The resulting suspension of freeze-dried liposomes containing SIZP in FCA is administered to animals being vaccinated.

Procedure 2. Water-Containing Formulation.

Method A. Alum Adjuvant.

SIZP is prepared as previously described (Brown, R. G., W. D. Bowen, J. D. Eddington, W. C. Kimmins, M. Mezei, J. L. Parsons, B. Pohajdak. (1997) Temporal trends in antibody production in captive grey seals, harp and hooded seals to a single administration immunocontraceptive vaccine. *J. Reproductive Immunology* 35:53–64, the disclosure of which is hereby incorporated by reference). The quantity of SIZP needed for the number of doses of the vaccine being prepared is weighed (the usual quantity of SIZP used for immunization is 50 µg for small animals and 100 µg for large animals). The SIZP is dissolved in pyrogen-free distilled water to give a final concentration of 2 mg/ml. An equal volume of ImjectAlum™ (an alum product from Pierce Chemical Co., catalogue # 77161) is added and the suspension is mixed, then freeze-dried.

To form liposomes, phospholipon 90 G (or other lipids selected from phosphoglycerol, phosphoethanolamine, phosphoserine, phosphocholine, phosphoinositol, etc. that form a closed lipid bilayer containing an entrapped aqueous volume) is weighed (0.1 g/dose of the vaccine composition). The phospholipon 90 G is mixed with cholesterol (0.01 g/dose of the vaccine composition) and the mixture is dissolved in chloroform:methanol (1/1;v/v; 1.5 ml/dose of the vaccine composition). Cholesterol can be replaced with other compounds that stabilize liposomes at concentrations determined by those skilled in the art. Washed glass beads (approximately 3 mm in diameter; 15 ml for 10 doses of the vaccine) are added and the mixture is evaporated under reduced pressure using a rotary evaporator until free of chloroform:methanol. To ensure removal of all chloroform:methanol, the mixture is placed in a dessicator under reduced pressure overnight at room temperature.

The freeze-dried SIZP/alum complex is suspended in saline (5 ml/mg SIZP) and the suspension is added to the flask containing the mixture of phospholipon 90 G/cholesterol coating the flask and glass beads. The contents of the flask are allowed to stand without agitation for 30 minutes. After 30 minutes, the flask is placed in a water bath at 35–40° C. and stirred gently with a spatula to form the liposomes. A microscope is used to evaluate liposome formation and stirring is continued with increased shaking until the mixture contains predominately multilamellar liposomes recognized by those skilled in the art. The aqueous suspension of liposomes (0.25 ml/dose for small animals and 0.5 ml/dose for large animals) is added to low viscosity mineral oil (0.25 ml oil/dose for small animals and 0.5 ml oil/dose for large animals) containing mannide oleate as an emulsifier (10:1:oil:emulsifier:v/v). The aqueous suspension of liposomes is added to the low mineral oil phase in aliquots with mixing between aliquots to maintain the continuous oil phase.

Method B. FCA Adjuvant.

Preparation of the vaccine composition to contain FCA as adjuvant in place of alum, is similar to method A, except SIZP by itself, rather than as a SIZP/alum complex, is encapsulated in liposomes as described above. The aqueous suspension of liposomes is added to FCA in aliquots with mixing between aliquots to maintain the continuous oil phase. The resulting aqueous suspension of liposomes containing SIZP in FCA is administered to animals being vaccinated.

Note: In some trials, the quantity of SIZP is varied to study the response of immunized animals to different quantities of antigen. In such experiments, the volume of the vaccine administered to small animals (cats, rabbits, etc.) was 0.5 ml and the volume administered to large animals (horses, fallow deer, white-tailed deer, etc.) was 1.0 ml. In such cases, the quantity of liposomes in each dose of the vaccine is maintained constant while the quantity of antigen encapsulated in liposomes varied.

Example 2

Immunization of Rabbits Against Native and Denatured Yeast Alcohol Dehydrogenase (ADH)

The vaccine composition is unique in producing high titers of anti-SIZP antibodies that are long-lasting following a single administration. To determine if the vaccine composition would produce high antibody titers with other antigens, particularly proteins that are not bound to cell membranes, rabbits are immunized with yeast alcohol dehydrogenase (ADH). Two forms of ADH are used as antigen, namely, native ADH and ADH that had been treated to denature the protein. To denature ADH, ADH is treated with mercaptoethanol (10% v/v in Tris buffer, 0.1 M, pH 7.5, 30 min, 100° C.). The solution is dialyzed against distilled water and freeze-dried. Four rabbits (2 for each treatment) are immunized with native or denatured ADH (40 µg) using a primary injection with Freund's complete adjuvant (FCA) followed by a booster injection with Freund's incomplete adjuvant (FIA) given one month later. The post-immunization period is considered to have begun after the booster injection. At the same time as the booster injection is administered, four rabbits (2 for each treatment) are immunized by single administration with either native or denatured ADH (40 µg) using the vaccine composition, that is ADH is encapsulated in liposomes that are suspended in saline (0.5 ml) and emulsified in FCA (0.5 ml). Anti-ADH titers are measured by ELISA using both native and denatured ADH (Table 2).

When rabbits are immunized with native ADH, the resulting serum contained similar quantities of anti-ADH antibodies when native ADH is delivered with the vaccine composition or by using a primary injection with one booster. In contrast, serum from rabbits immunized with denatured ADH delivered with the vaccine composition contain 2.7 times more antibody that bound to native ADH than serum from rabbits that are immunized with denatured ADH with a primary injection and one booster ($P<0.01$; $T=4.14$; $df=6$). In all cases, titers are higher in rabbits immunized with native ADH than when rabbits were immunized with denatured ADH. This indicates that native ADH is a better antigen than denatured ADH. Since many protein antigens are denatured to some degree during extraction and isolation or when produced by recombinant means, increased production of antibodies that bind better to native proteins can significantly improve the outcome of vaccination as demonstrated by immunocontraception of a variety of mammals with SIZP using the vaccine composition of the present invention.

Furthermore, anti-ADH sera from rabbits 237 and 238 recognize denatured ADH in Western blots with about 4–5 times the intensity of anti-ADH sera from rabbits 235 and 236. This confirms the results of titer measurements indicating that immunization of rabbits with the vaccine composition favours the production of anti-ADH antibodies that bind better to native ADH since many proteins are known to refold during the Western protocol to a more native state. This conclusion is supported by Muttilainen et al. (1995) in a study of Neisseria meningitidis outer membrane protein P1, who found antibodies to native P1 were elicited in mice vaccinated with denatured P1 constituted into phospholipid vesicles (liposomes). However, Muttilainen et al. (1995) did not use oil in their vaccine formulation, therefore, their immunization protocol was different than the present invention.

TABLE 2

Production of anti-ADH antibodies by rabbits immunized with native or denatured ADH delivered with and without liposome encapsulation

| Immunization | | | Anti-ADH titer (% of reference serum)[1] | | | |
|---|---|---|---|---|---|---|
| | | | Native ADH[3] | | Denatured ADH[3] | |
| Rabbit ID No. | Antigen | Delivery[2] | 4[4] | 5[4] | 4[4] | 5[4] |
| 231 | native ADH | −Liposomes | 187 | 148 | 19 | 23 |
| 232 | native ADH | −Liposomes | 200 | 161 | 17 | 15 |
| 233 | native ADH | +Liposomes | 239 | 156 | 21 | 14 |
| 234 | native ADH | +Liposomes | 100 | 100 | 19 | 11 |
| 235 | denatured ADH | −Liposomes | 41 | 37 | 7 | 3 |
| 236 | denatured ADH | −Liposomes | 30 | 18 | 7 | 4 |
| 237 | denatured ADH | +Liposomes | 101 | 71 | 8 | 3 |
| 238 | denatured ADH | +Liposomes | 101 | 63 | 12 | 7 |

[1]Anti-ADH serum from rabbit 234 is used as the reference serum.
[2]Native and denatured ADH are administered with the vaccine composition, that is encapsulated in liposomes with FCA as a single i.m. injection (+liposomes) or suspended in FCA followed one month later as a booster injection using FIA (−liposomes). Rabbits receive 40 µg ADH with each administration.
[3]ADH is purchased from Sigma Chemical Co. Denatured ADH is produced by treating native ADH with mercaptoethanol and heating to 100° C. for 30 minutes. The resulting denatured ADH contain three major proteins having molecular weights of 26, 33 and 40 kDa. Titers are measured by ELISA using native and denatured ADH as antigen to coat ELISA plates in separate determinations.
[4]Post-immunization in months.
Note: The reference serum noted in Table 2 is rabbit serum ID No. 234.

Example 3

Immunocontraception of Rabbits

Sera from rabbits immunized with a placebo vaccine that contained all ingredients of the vaccine composition except the antigen (porcine SIZP) contain no anti-porcine SIZP antibodies (see Table 3A). Immunization of rabbits with porcine SIZP (40 µg) encapsulated in liposomes containing phospholipon 90 G (0.1 g), cholesterol (0.01 g) in saline (0.5 ml) emulsified in FCA adjuvant (0.5 ml) produce high titers of anti-SIZP antibodies during the 12 month post-immunization monitoring period following a single administration of the vaccine. Immunization of rabbits with porcine SIZP (40 µg) encapsulated in liposomes with MF 59 adjuvant (0.5 ml) produce low anti-SIZP titers. In contrast, immunization of rabbits with porcine SIZP encapsulated in liposomes with alum adjuvant (100 µl, Pierce ImjectAlum™) produce anti-porcine SIZP titers that are less than titers produced using FCA in early post-immunization but the titers are less different than between the alum and FCA runs by the 12$^{th}$ month of post-immunization. Breeding of rabbits established that a single administration of the vaccine using FCA or alum reduces fertility of rabbits by 79 and 74% respectively (Table 3B). Immunization of rabbits by a single injection of SIZP (40 µg) that is not encapsulated in liposomes with Gerbu adjuvant produces low anti-porcine SIZP titers (Table 3A). As expected based on anti-SIZP titers, rabbits immunized with SIZP that are not encapsulated in liposomes with Gerbu adjuvant have the same fertility as rabbits that receive the placebo vaccine (Table 3B). These results indicate that vaccines comprising liposome-encapsulated antigen produce good results and that FCA and alum, particularly alum, are especially good adjuvants.

TABLE 3A

Effect of adjuvants on the production of anti-porcine SIZP antibodies by rabbits[1]
Post-immunization anti-porcine SIZP titer (% of reference)

| ID No. | 0 | 1 | 2 | 3 | 4 | 5 | 6 | 7 | 11 | 12 |
|---|---|---|---|---|---|---|---|---|---|---|
| Placebo | | | | | | | | | | |
| 2 | 0 | 1 | 0 | 0 | 0 | 0 | 0 | 0 | 0 | 0 |
| 13 | 0 | 0 | 0 | 0 | 0 | 0 | 0 | 0 | 0 | 0 |
| 14 | 0 | 0 | 0 | 0 | 0 | 0 | 0 | 0 | 0 | 0 |
| FCA | | | | | | | | | | |
| 3 | 0 | 145 | 112 | 94 | 82 | 45 | 23 | 24 | 20 | 20 |
| 15 | 0 | 100 | 71 | 68 | 83 | 19 | 29 | 26 | 18 | 25 |
| 16 | 0 | 125 | 111 | 122 | 128 | 111 | 74 | 92 | 75 | 63 |
| MF 59 | | | | | | | | | | |
| 1 | 0 | 3 | 1 | 1 | 1 | 2 | 0 | ND | ND | ND |
| 7 | 0 | 10 | 9 | 3 | 3 | 5 | 2 | ND | ND | ND |
| 19 | 0 | 12 | 6 | 3 | 3 | 3 | 3 | ND | ND | ND |
| 20 | 0 | 37 | 21 | 13 | 15 | 13 | 10 | ND | ND | ND |
| Alum | | | | | | | | | | |
| 11 | 0 | 19 | 12 | 12 | 11 | 14 | 18 | 7 | 8 | 10 |
| 12 | 0 | 20 | 10 | 10 | 8 | 6 | 11 | 5 | 2 | 4 |
| 23 | 0 | 31 | 16 | 40 | 22 | 20 | 33 | 28 | 37 | 28 |
| 24 | 0 | 36 | 21 | 40 | 27 | 24 | 40 | 36 | 34 | 34 |
| Gerbu without liposome encapsulation of SIZP | | | | | | | | | | |
| 9 | 0 | 5 | 2 | 1 | 1 | 1 | 1 | 1 | ND | ND |
| 10 | 0 | 11 | 3 | 3 | 2 | 2 | 3 | 1 | ND | ND |
| 21 | 0 | 17 | 4 | 6 | 19 | 5 | 6 | 2 | ND | ND |
| 22 | 0 | 24 | 3 | 6 | 3 | 4 | 4 | 7 | ND | ND |

[1]Rabbits receive a single administration of the placebo vaccine, vaccine that contained porcine SIZP (40 µg) encapsulated in liposomes (0.25 ml) with either FCA, MF 59 or alum adjuvants (0.25 ml) or vaccine that contained porcine SIZP (40 µg) dissolved in saline (0.25 ml) with gerbu adjuvant (0.25 ml). ND = not determined.

The reference serum used is from a rabbit immunized with porcine zona pellucida using a primary injection with Freund's complete adjuvant and 2 booster injections with Freund's incomplete adjuvant.

TABLE 3B

Effect of adjuvants on the fertility of rabbits immunized against porcine SIZP

| ID No | Live births/mating[1] | | | Average live births/mating | % reduction in fertility |
|---|---|---|---|---|---|
| | 1 | 2 | 3 | | |
| Placebo | | | | | |
| 2 | 6 | 0 | 4 | 5.1 | 0 |
| 13 | 7 | 1 | 10 | | |
| 14 | 6 | 7 | 5 | | |
| FCA | | | | | |
| 3 | 0 | 0 | 0 | 1.1 | 79 |
| 15 | 0 | 8 | 5 | | |
| 16 | 0 | NM | 0 | | |
| MF 59 | | | | | |
| 1 | 11 | NM | 10 | 6.1 | 0 |
| 7 | 0 | 0 | NM | | |
| 19 | 5 | 11 | 11 | | |
| 20 | 6 | 0 | 7 | | |
| Alum | | | | | |
| 11 | 0 | 0 | 6 | 1.3 | 74 |
| 12 | 0 | 0 | 0 | | |
| 23 | 0 | 0 | 0 | | |
| 24 | 3 | 5 | 2 | | |
| Gerbu without liposome encapsulation | | | | | |
| 9 | 0 | 0 | 11 | 5.3 | 0 |
| 10 | 0 | 0 | 0 | | |
| 21 | 8 | 9 | 11 | | |
| 22 | 10 | 7 | 11 | | |

NM = paired repeatedly with males without a successful mating
[1]Live births following a successful mating. The mating intervals were 65 ± 10, 141 ± 14 and 216 ± 14 days post-immunization for matings 1, 2 and 3 respectively.

Example 4

Immunocontraception in Cats

Twenty-nine specific pathogen free domestic short hair cats are housed at the specific pathogen free facility at the University of Florida under the supervision of Dr. Julie Levy and Mr. Shawn Gorman. Estrus cycling is monitored by daily observation and vaginal cytology. Vaccine compositions of the present invention, placebo vaccines and serum samples are coded as part of a double-blind study. The cats are divided randomly into 3 groups of nine or ten cats each. One group receives a placebo vaccine that contains all components of the vaccine composition except the antigen (porcine SIZP) by intramuscular injection. Each cat in this group receives liposomes containing no antigen in saline (0.25 ml) suspended in FCA (0.25 ml). Each cat in a second group of nine cats is immunized by intramuscular injection with the vaccine composition containing SIZP (135 μg) encapsulated in liposomes in saline (0.25 ml) and suspended in FCA (0.25 ml). Each cat in a third group of nine cats is immunized by intramuscular injection with the vaccine composition containing porcine SIZP (200 μg) with alum (0.12 ml, Pierce Chemical Co., catalogue number 77161) encapsulated in liposomes in saline (0.12 ml) and suspended in a suitable pharmacological carrier. Production of anti-SIZP antibodies in cats is measured by ELISA using protein A/alkaline phosphatase (Brown, R. G., W. D. Bowen, J. D. Eddington, W. C. Kimmins, M. Mezei, J. L. Parsons, B. Pohajdak. (1997) Temporal trends in antibody production in captive grey seals, harp and hooded seals to a single administration immunocontraceptive vaccine. *J. Reproductive Immunology* 35:53–64).

A single administration of the vaccine composition using FCA produces anti-SIZP antibody titers that reached maximal titers within 2 months (Table 4). The average two months post-immunization titer is 58±2% of the reference serum which decreased to 41±4% of the reference serum at four months post-immunization when a proven male cat is introduced to the colony. Cats that receive a single administration of the vaccine composition using alum as adjuvant produce anti-SIZP antibodies with an average titer of 67±2% of the reference serum two months post-immunization.

Monthly serum samples from cats that are immunized with the placebo vaccine containing all components of the vaccine composition except the antigen, have an average anti-SIZP titer of 0.6±0.2% of the reference serum during the post-immunization monitoring period. Therefore, it is apparent that cats that received the placebo vaccine will produce kittens during the post-immunization period.

TABLE 4

Production of anti-SIZP antibodies by cats immunized with the vaccine composition of the invention

| Cat ID | Anti-SIZP titer (% of reference serum) Post-immunization (months) | | | | | | | | | | | |
|---|---|---|---|---|---|---|---|---|---|---|---|---|
| No. | 0 | 1 | 2 | 3 | 4 | 5 | 6 | 7 | 8 | 9 | 10 | 11 |
| Placebo | | | | | | | | | | | | |
| 3 | 0 | 0 | 0 | 0 | 1 | 0 | 0 | 0 | 0 | 7 | 4 | 2 |
| 4 | 0 | 0 | 0 | 0 | 2 | 0 | 0 | 3 | 1 | 2 | 2 | 0 |
| 8 | 0 | 3 | 0 | 1 | 0 | 0 | 0 | 1 | 1 | 2 | 2 | 0 |
| 15 | 1 | 0 | 1 | 0 | 0 | 0 | 0 | 2 | 1 | ND | ND | ND |
| A | 0 | 0 | 3 | 0 | 1 | 0 | 0 | 0 | 0 | 2 | 2 | 0 |
| B | 0 | 0 | 0 | 1 | 1 | 1 | 0 | ND | 2 | 2 | 0 | 0 |
| E | 0 | 1 | 1 | 1 | 0 | 0 | 0 | 2 | 5 | ND | ND | ND |
| F | 0 | 1 | 1 | 0 | 0 | 0 | 0 | 2 | 0 | ND | ND | ND |
| I | 0 | 1 | 0 | 1 | 1 | 0 | 0 | 0 | 2 | 0 | 0 | ND |
| N | 0 | 1 | 0 | 0 | 1 | 1 | 1 | 2 | 1 | ND | ND | ND |
| Vaccine with FCA | | | | | | | | | | | | |
| 1 | 0 | 60 | 57 | 68 | 46 | 56 | 23 | 46 | 15 | 40 | 23 | 23 |
| 2 | 0 | 60 | 53 | 58 | 44 | 25 | 23 | 69 | 46 | 68 | 70 | 62 |
| 9 | 0 | 47 | 56 | 41 | 56 | 20 | 58 | 78 | 103 | 74 | 86 | ND |
| 13 | 0 | 42 | 64 | 53 | 66 | 55 | 47 | 29 | 33 | 12 | 16 | ND |
| 14 | 0 | 48 | 51 | 30 | 45 | 40 | 10 | 20 | 9 | 10 | 12 | 7 |
| C | 0 | 56 | 54 | 49 | 34 | 21 | 16 | 12 | 14 | 24 | 14 | 16 |
| D | 0 | 58 | 60 | 67 | 59 | 52 | 32 | 19 | 48 | ND | ND | ND |
| L | 0 | 47 | 61 | 40 | 28 | 16 | 46 | 37 | 59 | 70 | 59 | 72 |
| G | 0 | 59 | 65 | 79 | 85 | 81 | 92 | 94 | 96 | 115 | 152 | 79 |
| O | 0 | 48 | 42 | 53 | 42 | 24 | 26 | 28 | 25 | 31 | 16 | 10 |
| Vaccine with alum | | | | | | | | | | | | |
| 1P | 1 | 60 | 60 | 70 | 46 | 47 | 25 | 18 | 41 | 26 | 6 | ND |
| 1S | 0 | 73 | 56 | 43 | 24 | 42 | 19 | 18 | 18 | 14 | 4 | ND |
| 1T | 0 | 62 | 62 | 58 | 30 | 34 | 14 | 12 | 8 | 11 | 4 | ND |
| 1V | 2 | 70 | 68 | 60 | 40 | 36 | 12 | 12 | ND | ND | ND | ND |
| 1Y | 1 | 84 | 82 | 84 | 81 | 80 | 67 | 34 | 44 | 28 | ND | ND |
| 1Z | 0 | 77 | 75 | 71 | 54 | 72 | 54 | 26 | 35 | 21 | 9 | ND |
| Z1 | 0 | 61 | 74 | 95 | 83 | 100 | 98 | 92 | 70 | 42 | ND | ND |
| Z2 | 0 | 77 | 79 | 63 | 34 | 50 | 41 | 28 | 18 | 11 | ND | ND |
| Z3 | 0 | 65 | 72 | 61 | 55 | 30 | 35 | 18 | 20 | 6 | ND | ND |
| Z4 | 0 | 73 | ND | 68 | 53 | 29 | 32 | 17 | 12 | 13 | ND | ND |

ND = not determined

Example 5

Immunocontraception of Deer

Forty-one fallow deer (*Dama dama*) does on James Island, a 360-hectare island that lies off the coast of southern British Columbia, are immunized with the vaccine composition using FCA as adjuvant. Another group of forty fallow deer does are immunized with the vaccine composition using alum as the adjuvant. For capture, the deer are baited into a large (200×200 meter) pen that is connected to a series of fenced enclosures and a raceway that terminates in a small building. Before immunization, each deer is physically restrained and given a numbered ear tag, a colored plastic collar or radio collar with a mortality sensor, and a PIT (permanent identification transponder) tag bearing a unique code. Thus, if a treated deer loses all external marks, it could still be recognized as a treated animal from injury resulting from loss of ear tag and as a particular deer from the PIT tag. Each captive doe is injected intramuscularly in the rump with SIZP (100 μg) encapsulated in liposomes with FCA or alum adjuvants. Untreated does serve as controls.

Anti-SIZP titers are measured as previously described (Brown, R. G., W. D. Bowen, J. D. Eddington, W. C. Kimmins, M. Mezei, J. L. Parsons, B. Pohjajdak. (1997) Temporal trends in antibody production in captive grey seals, harp and hooded seals to a single administration immunocontraceptive vaccine. J. *Reproductive Immunology* 35:53–64) except that protein G/alkaline phosphatase replaced protein A/alkaline phosphatase since protein G has a higher affinity for fallow deer immunoglobulin than does protein A. Relative to the affinities of protein A and protein G for rabbit immunoglobulin (the reference serum), the affinities of protein A and protein G for fallow deer immunoglobulin are 8 and 89% respectively. Fallow deer anti-SIZP titers are uncorrected for relative affinity of protein G (Table 5A). None of the does examined 2 months or more following the rut and 8–9 months after being immunized with the vaccine containing FCA were pregnant, while 96% (192/200) untreated does are pregnant. Pregnancy is determined by examination of the reproductive tract for signs of pregnancy or by analyzing blood from live captured does for pregnancy-specific protein B (PSPB) by BioTracking, Inc. of Moscow, Id. (Willard et al., "Pregnancy detection and the effects of age, body weight, and previous reproductive performance on pregnancy status and weaning rates of farmed fallow deer (*Dama dama*). J. *Animal Science.* 77:32–38 (1999), the disclosure of which is hereby incorporated by reference). The contrast between the pregnancy rates of immunized and unimmunized does shows clearly that the vaccine composition containing FCA is effective in preventing conception. Since this is a multiple year study, as many as possible of the does are live captured.

TABLE 5A

Production of anti-SIZP antibodies by fallow deer immunized with the vaccine composition of the invention containing FCA adjuvant.

| Fallow deer ID No. | Post-immunization anti-SIZP titer (% of reference serum) Time (months) | | |
|---|---|---|---|
| | 0 | 1–2 | 7–10 |
| Controls | | | |
| 99023 | 0 | 0 | 0 |
| 99024 | 0 | 0 | 0 |

TABLE 5A-continued

Production of anti-SIZP antibodies by fallow deer immunized with the vaccine composition of the invention containing FCA adjuvant.

| Fallow deer ID No. | Post-immunization anti-SIZP titer (% of reference serum) Time (months) | | |
|---|---|---|---|
| | 0 | 1–2 | 7–10 |
| 99025 | 0 | 0 | 0 |
| 99027 | 0 | 0 | 0 |
| 99028 | 0 | 0 | 0 |
| 99029 | 0 | 0 | 0 |
| Vaccine with FCA | | | |
| 99026 | 0 | 117 | ND |
| 99025 | 0 | 72 | ND |
| 2000-06 | 0 | 96 | ND |
| 2000-08 | 0 | 94 | ND |
| 99007 | 0 | ND | 36 |
| 99008 | 0 | ND | 60 |
| 99009 | 0 | ND | 94 |
| 99016 | 0 | ND | 60 |
| 99017 | 0 | ND | 66 |
| 99019 | 0 | ND | 133 |
| 99020 | 0 | ND | 56 |

ND = not determined

Other experiments were performed on white-tailed deer. None of the white-tailed deer immunized with the vaccine composition comprising FCA became pregnant one year post-immunization. Only one of the white-tailed deer immunized with the vaccine composition comprising alum did not become pregnant one year post-immunization. The results for anti-SIZP titer levels are shown in Table 5B.

TABLE 5B

Production of anti-SIZP antibodies by white-tailed deer immunized with a composition of the present invention.

| White-tailed deer ID No. | Anti-SIZP (% of reference serum) Post-immunization (months) | | | | | |
|---|---|---|---|---|---|---|
| | 0 | 2 | 4 | 5 | 8 | 12 |
| Freund's complete adjuvant (FCA) | | | | | | |
| 19 | 0 | ND | ND | 85 | ND | |
| 21 | 0 | ND | ND | 139 | ND | |
| 33 | 0 | ND | ND | 125 | ND | |
| Alum | | | | | | |
| 949 | 1 | 12 | 11 | ND | 48 | 27 |
| 916 | 1 | 6 | 4 | ND | 5 | 2 |
| 744 | 3 | 105 | 111 | ND | 123 | 75 |
| 694 | 0 | 7 | 7 | ND | 5 | 4 |
| 956 | 0 | 5 | 4 | ND | 2 | 2 |
| 9 | 0 | ND | ND | 3 | ND | ND |
| 14 | 0 | ND | ND | 8 | ND | ND |
| 17 | 0 | ND | ND | 4 | ND | ND |
| 27 | 0 | ND | ND | 4 | ND | ND |

ND = not determined

Example 6

The Effect of Oil Content on the Production of Anti-SIZP Antibodies

The vaccine composition yields good antibody titers following a single administration of an antigen, therefore, unless stated otherwise all titers reported in the following example results from a single administration of the antigen in the vaccine formulation and other immunization protocols.

To determine if an aqueous phase is a necessary component of the vaccine composition to obtain a good immune response, three groups of rabbits (2 or 3 rabbits/group) are immunized with three different preparations of the vaccine containing SIZP (50 μg SIZP/rabbit) encapsulated in liposomes that are suspended in saline (0.5 ml) and emulsified in Freud's complete adjuvant (0.5 ml). The proportion of oil phase and water phase is equal in these preparations (Table (6A).

TABLE 6A

Effect of oil content of the vaccine composition on the production of anti-SIZP antibodies by rabbits

| Oil content | Anti-SIZP titer (% of reference serum)[1] Post-immunization (months) | | | | |
|---|---|---|---|---|---|
| (%, v/v) | 0 | 1 | 2 | 3 | 4 |
| 50[2] | 0 | 120 | 131 | 103 | 24 |
|  | 0 | 38 | 38 | 24 | 17 |
| 50[2] | 0 | 91 | 91 | 54 | 67 |
|  | 0 | 46 | 112 | 143 | 112 |
| 50[2] | 0 | 54 | 65 | 51 | ND |
|  | 0 | 95 | 94 | 81 | ND |
|  | 0 | 47 | 49 | 32 | ND |
| 100[3] | 0 | 61 | 75 | 136 | 34 |
|  | 0 | 14 | 24 | 100 | 95 |
| 100[4] | 0 | 159 | 149 | 215 | 27 |
|  | 0 | 50 | 196 | 244 | 128 |
| 100[4] | 0 | 11 | 30 | 48 | 29 |
|  | 0 | 15 | 28 | 40 | 41 |
| 100[4] | 0 | 54 | 54 | 90 | 91 |
|  | 0 | 14 | 2 | 19 | 19 |
|  | 0 | 47 | 49 | 67 | 76 |

[1]Each line presents titers of blood samples taken from the same rabbit.
[2]Liposomes containing SIZP (50 μg/rabbit) were suspended in saline (0.5 ml) and this aqueous phase was emulsified in Freund's complete adjuvant (0.5 ml).
[3]Liposomes containing SIZP (50 μg/rabbit) were freeze-dried and the resulting freeze-dried liposomes suspended in Freund's complete adjuvant (0.5 ml).
[4]Liposomes containing SIZP (50 μg/rabbit) are freeze-dried and the resulting freeze-dried liposomes suspended in Freund's complete adjuvant (0.2 ml).
ND = not determined.

The vaccine formulated to contain no water is used to immunize four groups of rabbits (2 or 3 rabbits/group) with four different preparations of the vaccine containing SIZP (50 μg SIZP/rabbit) encapsulated in freeze-dried liposomes suspended in Freund's complete adjuvant (0.2 ml or 0.5 ml). Since Freund's complete adjuvant contains no water, these preparations are water-free and contained only an oil phase. Average anti-SIZP titers 4 months post-immunization are 55±44% (coefficient of variation, cv 80%) for rabbits that are immunized with the composition containing 50% oil and 59±41% (cv 69%) for rabbits that are immunized with the vaccine containing 100% oil. There is no difference in response of female rabbits that received the vaccine with 100% oil and female rabbits that are immunized with the vaccine containing 50% oil (P=0.87; F (1,45)=0.03; average titers were 71±7% for 50% oil and 72±12% for 100% oil). These results indicate that the presence of an aqueous phase is not necessary for a good immune response to the vaccine.

To determine if there is a difference in duration of anti-SIZP titers in rabbits that are immunized with the vaccine composition with 50% and 100% oil, anti-SIZP titers are measured for 12 months (Table 6B). Anti-SIZP titers during the 12 month post-immunization period are similar in rabbits immunized with 50% oil formulation and the rabbit immunized with 100% oil formulation. To verify the biological effect of immunization with SIZP, proven female rabbits immunized with both formulations of the vaccine are mated with proven males 3 times during the 12 month post-immunization period. Reduction in fertility was 80% for the rabbits that are immunized with the vaccine containing 50% oil and the female rabbit that is immunized with the vaccine containing 100% oil produce no offspring indicating that the biological effect of reduced fertility is similar with both formulations of the vaccine.

TABLE 6B

Effect of oil content of the vaccine composition on the duration of anti-SIZP antibodies in rabbits

| Rabbit | Anti-SIZP titer (% of reference serum) Post-immunization (months) | | | | | | | | | |
|---|---|---|---|---|---|---|---|---|---|---|
| ID No. | 0 | 1 | 2 | 3 | 4 | 5 | 6 | 7 | 11 | 12 |
| 50% oil content |  |  |  |  |  |  |  |  |  |  |
| 3 | 0 | 145 | 112 | 94 | 82 | 45 | 23 | 24 | 20 | 20 |
| 15 | 0 | 100 | 71 | 68 | 83 | 19 | 29 | 26 | 18 | 25 |
| 16 | 0 | 125 | 111 | 122 | 128 | 111 | 74 | 92 | 75 | 63 |
| 100% oil content |  |  |  |  |  |  |  |  |  |  |
| 1 | 0 | 127 | 138 | ND | ND | ND | 33 | 51 | 17 | 27 |

ND = not determined.

Since liposomes are composed of material that is lipophilic, storage of liposomes in oil may lead to their destruction by dissolving the constituents of liposomes in the oil. To investigate this question, rabbits (2 rabbits in each group) are immunized with the vaccine (100% oil formulation) that is stored for up to 5 months at 5° C. and −20° C. Storage of the vaccine at 5° C. for 5 months reduced anti-SIZP titers of rabbits by only 28% (Table 6C; P=0.002; F (5,33)=4.9). Storage of the vaccine at −20° C. for 5 months reduced anti-SIZP titers by only 14% (Table 6D; P=<0.001; F (5,35)=23.7). These results indicate that most liposomes remain intact in oil since immunization of rabbits with a single injection of SIZP suspended in Freund's complete adjuvant without liposome encapsulation results in low titers (Table 6E).

TABLE 6C

Effect of storage of the vaccine composition with 100% oil formulation on the production of anti-SIZP antibodies by rabbits

| Storage[2] | Anti-SIZP titer[1] (% of reference serum) Post-immmunization (months) | | | | | | | |
|---|---|---|---|---|---|---|---|---|
| (months) | 0 | 1 | 2 | 3 | 4 | 5 | 6 | Average | SE |
| 0 | 0 | 60 | 123 | 112 | 163 | 109 | 119 | 114 | 11.2 |
|  | 0 | 26 | 108 | 112 | 163 | 131 | 141 |  |  |
| 1 | 0 | 26 | 112 | 183 | 121 | 122 | 100 | 113 | 11.9 |
|  | 0 | 77 | 133 | 142 | 117 | 70 | 153 |  |  |
| 2 | 0 | 63 | 176 | 128 | 70 | 127 | 57 | 98 | 13.9 |
|  | 0 | 50 | 110 | 100 | ND | ND | ND |  |  |
| 3 | 0 | 23 | 138 | 168 | 104 | 117 | 143 | 94 | 13.3 |
|  | 0 | 35 | 100 | 113 | 76 | 63 | 42 |  |  |

TABLE 6C-continued

Effect of storage of the vaccine composition with 100% oil formulation on the production of anti-SIZP antibodies by rabbits

| Storage[2] | Anti-SIZP titer[1] (% of reference serum) Post-immmunization (months) | | | | | | | | |
|---|---|---|---|---|---|---|---|---|---|
| (months) | 0 | 1 | 2 | 3 | 4 | 5 | 6 | Average | SE |
| 4 | 0 | 17 | 39 | 104 | 63 | 73 | 100 | 68 | 10.1 |
|   | 0 | 47 | 136 | 73 | 26 | 45 | 85 |   |   |
| 5 | 0 | 22 | 127 | 69 | 66 | 140 | 99 | 82 | 11.8 |
|   | 0 | 27 | 111 | 57 | 54 | 140 | 74 |   |   |

[1]The vaccine composition (100% oil formulation) is placed in biobullets purchased from Ballistivet ™ and surgically implanted intramuscularly into rabbits.
[2]Biobullets are stored at 5° C.

TABLE 6D

Effect of storage of the vaccine composition with 100% oil formulation on the production of anti-SIZP antibodies by rabbits

| Storage[2] | Anti-SIZP titer[1] (% of reference serum) Post-immunization (months) | | | | | | | | |
|---|---|---|---|---|---|---|---|---|---|
| (months) | 0 | 1 | 2 | 3 | 4 | 5 | 6 | Average | SE |
| 0 | 0 | 60 | 123 | 112 | 163 | 109 | 119 | 114 | 11.2 |
|   | 1 | 26 | 108 | 112 | 163 | 131 | 141 |   |   |
| 1 | 0 | 9 | 13 | 13 | 41 | 19 | 60 | 27 | 6.7 |
|   | 0 | 6 | 16 | 14 | 73 | 33 | ND |   |   |
| 2 | 0 | 9 | 14 | 23 | 70 | 136 | 116 | 51 | 12.7 |
|   | 0 | 6 | 30 | 19 | 41 | 95 | 57 |   |   |
| 3 | 0 | 13 | 23 | 127 | 100 | 73 | 88 | 57 | 11.1 |
|   | 0 | 13 | 18 | 90 | 61 | 58 | 30 |   |   |
| 4 | 0 | 13 | 68 | 50 | 71 | 80 | 122 | 85 | 14.0 |
|   | 0 | 13 | 114 | 134 | 81 | 100 | 179 |   |   |
| 5 | 0 | 9 | 114 | 75 | 87 | 146 | 92 | 98 | 13.7 |
|   | 1 | 22 | 108 | 116 | 109 | 179 | 125 |   |   |

[1]The vaccine composition (100% oil formulation) is placed in biobullets purchased from Ballistivet ™ and surgically implanted intramuscularly into rabbits.
[2]Biobullets are stored at −20° C.

TABLE 6E

Production of anti-SIZP antibodies by rabbits immunized with a single administration of SIZP without encapsulation of SIZP in liposomes

| Rabbit ID No. | Anti-SIZP titer (% of reference serum)[1] Post-immunization (months) | | | | |
|---|---|---|---|---|---|
|   | 0 | 1 | 2 | 3 | 4 |
| 1 | 0 | 43 | 19 | 9 | 2 |
| 2 | 0 | 27 | 7 | 4 | 1 |

[1]Rabbits are immunized with a single administration of SIZP (50 μg/rabbit) suspended in Freund's Complete Adjuvant.

To determine if the vaccine formulated to contain no aqueous phase would result in a good response in another mammalian species, grey seals (*Halichoerus grypus*) are immunized with the vaccine containing either equal oil and aqueous phases, only an aqueous phase, or only an oil phase (Table 6F). There was no difference in anti-SIZP titers in the vaccine that contained equal oil and aqueous phases or only oil but administration of the vaccine that contained all ingredients except oil, resulted in significantly lower titers.

TABLE 6F

Effect of oil content of the vaccine composition on the production of anti-SIZP antibodies by grey seals.

| Oil content | Anti-SIZP titer (% of reference serum)[1] Post-immunization (months) | | | | |
|---|---|---|---|---|---|
| (%, v/v) | 0 | 1 | 2 | 3 | 4 |
| 0[2] | 0 | 5 | 4 | 1 | 1 |
|   | 0 | 1 | 2 | 1 | 1 |
| 50[3] | 0 | 7 | 9 | 145 | 107 |
|   | 0 | 41 | 52 | 82 | 38 |
| 100[4] | 0 | 20 | 28 | 79 | 60 |
|   | 0 | 3 | 30 | 90 | 50 |

[1]Each line presents titers of blood samples taken from the same grey seal.
[2]Liposomes containing SIZP (100 μg/grey seal) and heat killed *Mycobacterium tuberculosis* (2 mg/grey seal), the active ingredient in Freund's complete adjuvant as supplied by Sigma Chemical Co. and used in all studies reported herein are suspended in saline (0.5 ml).
[3]Liposomes containing SIZP (100 μg/grey seal) are suspended in saline (0.5 ml) and this aqueous phase is emulsified in Freund's complete adjuvant (0.5 ml).
[4]Liposomes containing SIZP (100 μg/grey seal) are freeze-dried and the resulting freeze-dried liposomes suspended in Freund's complete adjuvant (0.5 ml).

Example 7

Use of Archaebacterial Lipids in Liposomes

Liposomes are completely closed lipid membranes that can be made from a variety of lipid materials. In this example, liposomes made using archaebacterial lipids are compared to liposomes made using soybean lecithin for their ability to stimulate antibody production by rabbits (Table 7). Liposomes made with soybean lecithin result in better production of anti-SIZP antibodies than liposomes made with archaebacterial lipids.

TABLE 7

Production of anti-SIZP antibodies by rabbits immunized with liposomes prepared with archaebacterial lipids or soybean lecithin.

| ID No. | Type of lipid | Anti-SIZP titer (% of reference serum) Post immunization (months) | | | | | |
|---|---|---|---|---|---|---|---|
|   |   | 0 | 1 | 2 | 3 | 4 | 5 |
| 112 | Soybean lecithin | 0 | 143 | 195 | 137 | 197 | 98 |
| 115 | Soybean lecithin | 0 | 200 | 198 | 157 | 179 | 106 |
| 117 | Archaebacterial lipids | 0 | 46 | 30 | 37 | 13 | ND |
| 118 | Archaebacterial lipids | 0 | 7 | 4 | 8 | 2 | ND |

ND = not determined.

Example 8

Immunization Against Streptokinase

The vaccine composition is unique in producing high titers of anti-SIZP antibodies that are long-lasting following a single administration. To determine if the vaccine composition would produce high antibody titers with other antigens, rabbits are immunized with streptokinase.

Streptokinase is an exoprotein produced by pathogenic strains of the Streptococci family of bacteria. As an activator of vascular fibrinolysis its therapeutic usefulness has been appreciated for many years in the treatment of myocardial infarction. Streptokinase unfolds in a non-cooperative manner. Therefore, the protein can assume a number of partially folded states that contain some regions that appear to be native and others that are unfolded. Three domains of different stability exist that are independent of other regions of the protein (Teuten et al., 1993, Biochem. J. 290:313–319). Native streptokinase contains immunodominant epitopes in the C-terminal region (Torrens et al., 1999, Immunology Letters 70:213–218). The C-terminal region is relatively unstructured (Parrado et al., 1996, Protein Sci 5:693–704) therefore heat treatment cannot alter the structure since it was unstructured before heat treatment. The thermal stability of domain C is significantly increased by its isolation from the rest of the chain (Connejero-Lara et al., 1996, Protein Sci 5:2583–2591). Loss of the C-terminal region results in a less immunogenic protein but does expose immunogenic epitopes hidden in the native molecule. In our studies, the C-terminal region was present in native and heat-treated streptokinase, therefore, as the immunodominant region of the protein, it would, determine the response of the rabbits. If the C-terminal region retained the same epitopes following heat treatment as found in the native state, one would not expect to find a difference in binding of anti-streptokinase antibodies to native and heat-treated streptokinase. These are exactly the observations found (Table 8). We have proposed that delivery of denatured proteins using a vaccine composition of the present invention favours the production of antibodies directed against native epitopes. This is supported by the studies of alcohol dehydrogenase in Example 2. The results with streptokinase are consistent with this proposal since heat treatment would not alter the structure of the immunodominant region and the prediction follows that there would be no difference in the immune response of rabbits being immunized with native and heat treated streptokinase regardless of the delivery system employed. These are precisely our observations (Table 8).

TABLE 8

Epitope mapping of rabbit anti-streptokinase sera from rabbits immunized with native and heat-treated streptokinase (100° C. for 10 minutes in 5% mercaptoethanol) using conventional immunization protocols[1] or the method of the present invention[2].

| | | | Titer (% of reference serum)[3] | | | | | |
|---|---|---|---|---|---|---|---|---|
| Immunization | | | Native streptokinase | | | Heat-treated streptokinase | | |
| Rabbit | | | Post-immunization (months) | | | | | |
| ID | Antigen | Delivery | 0 | 1 | 2 | 0 | 1 | 2 |
| 21 | Native | Invention | 0 | 100 | 122 | 0 | 98 | 122 |
| 24 | Native | Invention | 0 | 82 | 98 | 0 | 53 | 108 |
| 25 | Native | Conventional | 0 | 10 | 89 | 0 | 8 | 100 |
| 20 | Native | Conventional | 0 | 9 | 94 | 0 | 3 | 92 |
| 23 | Heat-treated | Invention | 0 | 10 | 34 | 0 | 15 | 31 |
| 28 | Heat-treated | Invention | 0 | 25 | 99 | 0 | 24 | 94 |
| 27 | Heat-treated | Conventional | 0 | 9 | 107 | 0 | 7 | 94 |
| 30 | Heat-treated | Conventional | 0 | 10 | 100 | 0 | 8 | 94 |

[1]Rabbits were immunized with 75 μg streptokinase in Freund's complete adjuvant followed by one booster injection one month later with 75 μg streptokinase in Freund's incomplete adjuvant.
[2]Rabbits were immunized with a single injection of 75 μg streptokinase in a vaccine of the present invention.
[3]Titers were measured with both native and heat-treated streptokinase.

It is evident from the results that a single injection of streptokinase using a vaccine of the present invention produced anti-streptokinase titers similar to titers obtained by the conventional primary and booster injection protocols. Also, regardless of the immunization protocol used, that is the present invention or conventional, the antibodies produced bound to native and heat-treated streptokinase equally well.

Example 9

Use of an Edible Vegetable Oil

A vaccine composition was formulated in accordance with this invention using Canola oil in place of mineral oil. The results are shown in Table 9. The results indicate that vaccines formulated with Canola oil produce anti-SIZP antibodies in rabbits, therefore, Canola oil is useful. However, the titer levels are not as high as with mineral oil.

TABLE 9

Effect of Canola oil on production of anti-SIZP antibodies in rabbits

| Rabbit | Vaccine | Anti-SIZP titer (% of reference serum) Post-immunization (months) | | | | | | | |
|---|---|---|---|---|---|---|---|---|---|
| ID | formulation | 0 | 1 | 2 | 3 | 4 | 5 | 6 | 7 |
| 4 | Alum/mineral oil | 0 | 111 | 123 | 105 | 124 | 95 | 125 | 157 |
| 14 | | 0 | 231 | 132 | 205 | 178 | 279 | 258 | 251 |
| 9 | FCA/mineral oil[1] | 0 | 162 | 264 | 310 | ND | ND | ND | ND |
| 26 | | 0 | 351 | 166 | 112 | ND | ND | ND | ND |

TABLE 9-continued

Effect of Canola oil on production of anti-SIZP antibodies in rabbits

| Rabbit ID | Vaccine formulation | Anti-SIZP titer (% of reference serum) Post-immunization (months) | | | | | | | |
|---|---|---|---|---|---|---|---|---|---|
| | | 0 | 1 | 2 | 3 | 4 | 5 | 6 | 7 |
| 34 | FCA/Canola oil[2] | 0 | 27 | 24 | 37 | ND | ND | ND | ND |
| 36 | | 0 | 18 | 24 | 36 | ND | ND | ND | ND |

[1]Freund's complete adjuvant (FCA) was obtained from a commercial source (Sigma) and was formulated with mineral oil.
[2]FCA/Canola oil contained the same quantity of Mycobacterium heat-killed cells as present in FCA but the mineral oil component of FCA was replaced with edible Canola oil.
ND = not determined Example 10

Immunization Against Hepatitis B

A hepatitis B vaccine was formulated in accordance with the present invention using 5 micrograms hepatitis B surface antigen (Recombivax HB™, a recombinant hepatitis B antigen) containing alum adjuvant encapsulated in liposomes containing soybean lecithin (0.05 g) and cholesterol (0.005 g) suspended in saline (0.25 ml) then emulsified in low viscosity mineral oil (0.225 ml) and mannide oleate (0.025 ml). A conventional hepatitis B vaccine using 5 micrograms hepatitis B surface antigen (Recombivax HB™) containing alum adjuvant in a volume of 0.5 ml aqueous medium as recommended by the manufacturer was also administered. Eight rabbits were immunized with the vaccine prepared in accordance with the present invention and eight rabbits were immunized with the conventional vaccine. Results are shown in Table 10.

It is evident from Table 10 that the vaccine prepared in accordance with the present invention results in about 6 times more antibody 1 month post-immunization than conventional delivery of hepatitis B surface antigen.

TABLE 10

Production of anti-HepB antibodies by rabbits immunized with a commercial HepB vaccine or with a HepB vaccine formulated in accordance with the present invention

| Rabbit ID | Anti-HepB titer (mlU/ml)[1] Post-immunization (months) | |
|---|---|---|
| | 0 | 1 |
| Commercial vaccine | | |
| 96 | 0 | 736 |
| 101 | 0 | 1237 |
| 97 | 0 | 488 |
| 100 | 0 | 1877 |
| 99 | 0 | 6251 |
| 103 | 0 | 8384 |
| 98 | 0 | 688 |
| 102 | 0 | 1568 |
| Average | 0 | 2654 |
| Vaccine of the invention | | |
| 93 | 0 | 32,341 |
| 95 | 0 | 3371 |
| 88 | 0 | 5717 |
| 81 | 0 | 23,808 |
| 83 | 0 | 9344 |
| 84 | 0 | 17,856 |
| 79 | 0 | 9344 |
| 85 | 0 | 21,675 |
| Average | 0 | 15,432 |

[1]Antibody titers were measured using the enzyme immunoassay for the detection of antibody to hepatitis B surface antigen (anti-HBs) distributed by DiaSorin Inc., Stillwater, MN, USA.

Example 11

Effect of Formulating Vaccines with Alum Adjuvant Inside and Outside of Liposomes Vaccines were prepared as follows:

| Group | SIZP antigen | Alum | Medium |
|---|---|---|---|
| 1 | inside liposome | inside liposome | saline |
| 2 | inside liposome | outside liposome | saline |
| 3 | inside liposome | inside liposome | oil |
| 4 | inside liposome | outside liposome | oil |
| 5 | control-no liposomes | | oil |
| 6 | control-no liposomes | | saline |

Group 1–4 were prepared with 100 μg SIZP encapsulated in liposomes formed with 0.1 g soybean lecithin and 0.01 g cholesterol. The liposomes in Groups 1 and 3 also contained 100 μm ImjectAlum™. In Groups 2 and 4, 100 μl ImjectAlum™ was placed outside the liposomes. In Groups 1 and 2, the liposomes were suspended in 0.25 ml saline and this suspension emulsified in 0.225 ml low viscosity mineral oil and 0.025 ml mannide oleate. In Groups 3 and 4, the liposomes were freeze dried then suspended in 0.225 ml low viscosity mineral oil and 0.025 ml mannide oleate and this suspension emulsified in 0.25 ml saline. In Group 5, 100 μg SIZP and 100 μl ImjectAlum™ were freeze dried, then suspended in 0.225 ml low viscosity mineral oil and 0.025 ml mannide oleate and emulsified in 0.25 ml saline. In Group 6, 100 μg SIZP and 100 μl ImjectAlum™ were freeze dried, then suspended in 0.25 ml saline and emulsified in 0.225 ml low viscosity mineral oil and 0.025 ml mannide oleate. Rabbits were immunized with the six groups of vaccines and the results are shown in Table 11.

TABLE 11

Production of anti-SIZP antibodies by rabbits immunized with four formulations
of a vaccine of the present invention containing alum adjuvant (Groups 1–4)
and two control formulations containing alum adjuvant (Groups 5–6)

| Group | Rabbit ID | Anti-SIZP titer (% reference serum) Post-immunization months | | | | Average titer Post-immunization months | | | | Standard Error of average titer | | |
|---|---|---|---|---|---|---|---|---|---|---|---|---|
| | | 0 | 1 | 2 | 3 | 0 | 1 | 2 | 3 | 1 | 2 | 3 |
| 1 | 49 | 2 | 107 | 176 | 183 | 0 | 135 | 203 | 236 | 22 | 28 | 37 |
| 1 | 76 | 0 | 134 | 105 | 124 | | | | | | | |
| 1 | 71 | 0 | 70 | 249 | 331 | | | | | | | |
| 1 | 82 | 0 | 182 | 236 | 268 | | | | | | | |
| 1 | 78 | 0 | 182 | 249 | 274 | | | | | | | |
| 2 | 73 | 0 | 373 | 273 | 304 | 0 | 287 | 207 | 258 | 32 | 24 | 15 |
| 2 | 42 | 0 | 328 | 199 | 281 | | | | | | | |
| 2 | 62 | 0 | 259 | 194 | 244 | | | | | | | |
| 2 | 77 | 0 | 182 | 131 | 235 | | | | | | | |
| 2 | 74 | 0 | 295 | 238 | 225 | | | | | | | |
| 3 | 63 | 0 | 363 | 135 | 113 | 0 | 300 | 171 | 160 | 32 | 26 | 34 |
| 3 | 67 | 0 | 286 | 175 | 140 | | | | | | | |
| 3 | 70 | 0 | 332 | 241 | 261 | | | | | | | |
| 3 | 80 | 0 | 218 | 131 | 125 | | | | | | | |
| 4 | 48 | 0 | 383 | 210 | 113 | 0 | 200 | 138 | 108 | 49 | 20 | 12 |
| 4 | 64 | 0 | 129 | 109 | 121 | | | | | | | |
| 4 | 61 | 0 | 125 | 98 | 63 | | | | | | | |
| 4 | 60 | 0 | 148 | 140 | 115 | | | | | | | |
| 4 | 66 | 0 | 215 | 134 | 130 | | | | | | | |
| 5 | 45 | 0 | 21 | 133 | 120 | 0 | 26 | 96 | 123 | 8 | 29 | 33 |
| 5 | 65 | 0 | 6 | 26 | 42 | | | | | | | |
| 5 | 69 | 0 | 49 | 110 | 121 | | | | | | | |
| 5 | 72 | 0 | 12 | 36 | 89 | | | | | | | |
| 5 | 50 | 0 | 40 | 176 | 242 | | | | | | | |
| 6 | 68 | 0 | 28 | 31 | 22 | 0 | 16 | 22 | 18 | 4 | 3 | 1 |
| 6 | 75 | 0 | 9 | 16 | 16 | | | | | | | |
| 6 | 46 | 0 | 18 | 23 | 17 | | | | | | | |
| 6 | 43 | 0 | 10 | 19 | 16 | | | | | | | |

Example 12

Effect of Formulating Vaccines with Heat Killed *Mycobacterium tuberculosis* Adjuvant Inside and Outside of Liposomes Vaccines were prepared as follows:

| Group | SIZP antigen | Heat-killed *M. tuberculosis* | Medium |
|---|---|---|---|
| 1 | inside liposome | inside liposome | saline |
| 2 | inside liposome | outside liposome | saline |
| 3 | inside liposome | inside liposome | oil |
| 4 | inside liposome | outside liposome | oil |

Groups 1–4 were prepared with 100 μg SIZP encapsulated in liposomes formed with 0.1 g soybean lecithin and 0.01 g cholesterol. The liposomes in Groups 1 and 3 also contained 200 μg heat killed *M. tuberculosis*. In Groups 2 and 4, 200 μg heat killed *M. tuberculosis* was placed outside the liposomes. In Groups 1 and 2, the liposomes were suspended in 0.2 ml saline and this suspension emulsified in 0.18 ml low viscosity mineral oil and 0.02 ml mannide oleate. In Groups 3 and 4, the liposomes were freeze dried then suspended in 0.18 ml low viscosity mineral oil and 0.02 ml mannide oleate and this suspension emulsified in 0.2 ml saline. Rabbits were immunized with the four groups of vaccines and the results are shown in Table 12.

TABLE 12

Production of anti-SIZP antibodies by rabbits immunized with
four formulations of a vaccine of the present invention
containing heat killed M. tuberculosis

| Group | Rabbit ID | Anti-SIZP titer (% reference serum) Post-immunization months | | | | Average titer Post-immunization months | | | | Standard Error of average titer | | |
|---|---|---|---|---|---|---|---|---|---|---|---|---|
| | | 0 | 1 | 2 | 3 | 0 | 1 | 2 | 3 | 1 | 2 | 3 |
| 1 | 33 | 0 | 245 | 236 | 259 | 0 | 318 | 262 | 437 | 51 | 18 | 126 |
| 1 | 29 | 0 | 390 | 288 | 614 | | | | | | | |
| 2 | 32 | 0 | 544 | 515 | 633 | 0 | 576 | 532 | 638 | 22 | 12 | 3 |

TABLE 12-continued

Production of anti-SIZP antibodies by rabbits immunized with four formulations of a vaccine of the present invention containing heat killed M. tuberculosis

| Group | Rabbit ID | Anti-SIZP titer (% reference serum) Post-immunization months | | | | Average titer Post-immunization months | | | | Standard Error of average titer | | |
|---|---|---|---|---|---|---|---|---|---|---|---|---|
| | | 0 | 1 | 2 | 3 | 0 | 1 | 2 | 3 | 1 | 2 | 3 |
| 2 | 22 | 0 | 608 | 549 | 642 | | | | | | | |
| 3 | 9  | 0 | 162 | 264 | 310 | 0 | 293 | 599 | 508 | 93 | 237 | 140 |
| 3 | 13 | 0 | 424 | 933 | 707 | | | | | | | |
| 4 | 16 | 0 | 454 | 276 | 532 | 0 | 403 | 221 | 322 | 36 | 39 | 149 |
| 4 | 26 | 0 | 351 | 166 | 112 | | | | | | | |

Example 13

Immunization of Rabbits with Native and Denatured Yeast Alcohol Dehydrogenase (ADH) Together with Alum Adjuvant Vaccines of the present invention were formulated containing 100 μg of native or denatured ADH together with 100 μl ImjectAlum™ encapsulated in liposomes formed with 0.1 g soybean lecithin and 0.01 g cholesterol. The liposomes were suspended in 0.25 ml saline and the suspension emulsified in 0.225 ml low viscosity mineral oil and 0.025 ml mannide oleate.

Conventional vaccines were formulated containing 100 μg of native or denatured ADH together with 100 μl ImjectAlum™ and suspended in 0.5 ml saline.

Denatured ADH was prepared by heating ADH to 100° C. for 30 minutes and treating with 10% mercaptoethanol for 30 minutes at room temperature to cleave disulfide bonds. Mercaptoethanol was removed by dialysis for 12 hours and denatured ADH was recovered by freeze drying.

Results comparing the vaccines of the present invention to the conventional vaccines are shown in Table 13.

TABLE 13

Production of anti-ADH antibodies by rabbits immunized with native and denatured ADH using alum as adjuvant

| Rabbit ID | Delivery System | Anti-ADH titer (% reference serum) Post-immunization (months) | | | | | | | |
|---|---|---|---|---|---|---|---|---|---|
| | | Native ADH | | | | Denatured ADH | | | |
| | | 0 | 1 | 2 | 3 | 0 | 1 | 2 | 3 |
| Native ADH | | | | | | | | | |
| 54 | invention | 0 | 24 | 42 | 66 | 0 | 8 | 4 | 4 |
| 57 | | 0 | 100 | 143 | 146 | 0 | 29 | 3 | 6 |
| 55 | | 0 | 91 | 85 | 111 | 0 | 26 | 3 | 5 |
| 40 | conventional | 0 | 1 | 1 | 2 | 0 | 1 | 0 | 1 |
| 44 | | 0 | 1 | 1 | 1 | 0 | 1 | 0 | 1 |
| 47 | | 0 | 5 | 4 | 8 | 0 | 3 | 1 | 1 |
| Denatured ADH | | | | | | | | | |
| 53 | invention | 0 | 1 | 2 | 5 | 0 | 1 | 1 | 2 |
| 58 | | 0 | 1 | 1 | 2 | 0 | 1 | 0.5 | 1 |
| 52 | | 0 | 1 | 4 | 15 | 0 | 1 | 0.5 | 1 |
| 51 | conventional | 0 | 2 | 4 | 4 | 0 | 1 | 0.5 | 2 |
| 59 | | 0 | 1 | 1 | 4 | 0 | 1 | 0.5 | 0 |
| 56 | | 0 | 2 | 2 | 2 | 0 | 1 | 0.5 | 0 |

The results show that delivery of native or denatured ADH using a formulation of the present invention results in an increased production of anti-ADH antibodies compared to the production of anti-ADH antibodies by rabbits immunized against native or denatured ADH using conventional methods. Furthermore, rabbits immunized with denatured ADH produced more antibodies directed against native ADH when a formulation of the present invention is used rather than when denatured ADH is delivered by conventional means with no booster injections.

Example 14

Epitope Mapping

Epitope mapping experiments to demonstrate that vaccines of the present invention produce antibodies having different binding specificity for an antigen than achieved by conventional immunization protocols of primary and secondary booster injections. Fragments of the ZP antigen were specifically used but it is expected that other antigens will behave in a similar manner.

Conventional immunization of grey and harp seals with a primary injection and two booster injections results in low anti-SIZP antibody titers that peak two months post-immunization in both grey and harp seals. In contrast, immunization with a vaccine formulated in accordance with the present invention produces anti-SIZP antibody titers that persist for at least 24 months in grey seals and 5–6 months in harp seals, with one exception. Titers in harp seals reach a plateau that persist for 6–10 months post-immunization. Therefore, a vaccine formulated in accordance with the present invention induces high anti-SIZP titers with long duration compared to conventional immunization protocols using primary and booster injections.

The polypeptide fragments of ZPB and ZPC that were used in epitope mapping to demonstrate that anti-SIZP antibodies produced following conventional immunization protocols have a different binding specificity than anti-SIZP antibodies produced following immunization with a vaccine of the present invention are shown in FIG. 1. The fragments ZPB1, ZPB2, ZPC1 and ZPC2 are short length polypeptides and do not have the three-dimensional structures of full length ZPB and ZPC. In FIG. 1, the full-length unprocessed polypeptides are shown above the two ZPB and ZPC fragments. The secretory signal peptides that are cleaved in the native proteins are shaded in black.

Anti-SIZP grey seal antibodies produced following conventional immunization (a primary and two booster injections using FCA adjuvant) have a high affinity for the ZPB1, ZPB2, ZPC1 and ZPC2 fragments (Table 14A, seal ID 1). In contrast, grey seals immunized with a vaccine formulated in accordance with the present invention (Table 14A, seal ID 76 and 96) produce antibodies that have a low affinity for fragments ZPB2, ZPC1 and ZPC2 one year post-immunization and low affinity for all four fragments three years post-immunization. The four fragments together account for 80% of the protein found in SIZP.

TABLE 14A

Epitope mapping of grey seal anti-SIZP antibodies using recombinant fragments of ZPB and ZPC produced in E. coli

| Seal ID | Post-immunization (months) | Binding relative to SIZP (%) | | | | |
|---------|---------------------------|------|------|------|------|-------|
|         |                           | ZPB1 | ZPB2 | ZPC1 | ZPC2 | Total |
| 1       | 3                         | 30   | 44   | 59   | 41   | 174   |
| 1       | 4                         | 71   | 70   | 83   | 63   | 287   |
| 76      | 12                        | 54   | 25   | 8    | 12   | 99    |
| 76      | 36                        | 18   | 9    | 13   | 11   | 51    |
| 96      | 12                        | 47   | 18   | 15   | 10   | 90    |
| 96      | 36                        | 10   | 8    | 15   | 10   | 43    |

A temporal study of the binding specificity of antibodies produced by grey seals immunized with a vaccine formulated in accordance with the present invention indicated that antibodies produced early post-immunization (<7 months) bind to epitopes found predominantly on the ZPB1 fragment. Antibodies produced late post-immunization (>7 months) have lower affinity for ZPB1 and the other three fragments. ZPB1, ZPB2, ZPC1 and ZPC2 are low molecular weight and are not glycosylated. These fragments have less three-dimensional structure than full-length ZPB and ZPC because of their low molecular weight. Therefore, antibodies that bind to SIZP but not ZPB1, ZPB2, ZPC1 or ZPC2 must either be recognizing three-dimensional structures found only on full-length ZPB and ZPC or the carbohydrate covalently linked to these proteins. Since the total amount of antibody bound to the fragments early post-immunization exceeds or is equivalent to the amount of antibody binding to ZPB and ZPC, carbohydrate-recognizing antibody must have a minor role. This implies that 3-D structures determine the difference in binding to the fragments as opposed to SIZP. A survey of nine other grey seals immunized with SIZP in a vaccine of the present invention indicates similar reduction to antibodies produced 5 months or more post-immunization.

In another experiment, three of four rabbits immunized with a vaccine of the present invention produced antibodies with a higher affinity for epitopes in ZPB1 than in the other three fragments. Only 20–40% of the antibodies produced by all four rabbits bound to epitopes found in the four ZP fragments. Therefore, 60–80% of the anti-SIZP antibodies produced by rabbits immunized with a vaccine of the present invention bound only to epitopes found in full length ZPB and ZPC. Therefore, 60–80% of antibodies produced in rabbits immunized with a vaccine of the present invention recognize epitopes related to native 3-D structures.

In yet another experiment, immunization of harp seals (156 and 162) by conventional protocols of a primary injection using FCA adjuvant followed by booster injections with FIA adjuvant produced antibodies early post-immunization that bound to epitopes found in ZPB1, ZPB2 and ZPC2 (harp seal 156) or all four fragments (harp seal 162) as well as in SIZP (Table 14B). In contrast, immunization of harp seal 151 with a vaccine formulated in accordance with the present invention produced antibodies early post-immunization (<5 months) that bound to epitopes found in all four ZP fragments but antibodies produced late post-immunization (>7 months) bound to epitopes found only on full length ZPB and ZPC (Table 14B). Only 30–40% of the antibodies produced by immunization of harp seal 153 with a vaccine of the present invention bound well to epitopes on the four ZP fragments, implying that 60–70% of the antibodies produced by harp seal 153 during the 7 month post-immunization period bound only to epitopes found in full length ZPB and ZPC. These epitopes must be related to structures found only in full length ZPB and ZPC implying 3-D structures. Immunization of hooded seal 1 with a vaccine of the present invention produced antibodies with a similar temporal sequence of specificity as harp seal 151.

TABLE 14B

Epitope mapping of harp and hooded seal anti-SIZP antibodies using recombinant fragments of ZPB and ZPC produced in E. coli

| Seal ID  | Post-immunization (months) | Binding relative to SIZP (%) | | | | |
|----------|---------------------------|------|------|------|------|-------|
|          |                           | ZPB1 | ZPB2 | ZPC1 | ZPC2 | Total |
| Harp 156 | 2                         | 9    | 8    | 7    | 7    | 31    |
|          | 3                         | 30   | 19   | 10   | 24   | 83    |
|          | 4                         | 36   | 38   | 2    | 34   | 110   |
| Harp 162 | 2                         | 8    | 10   | 11   | 11   | 40    |
|          | 3                         | 33   | 26   | 19   | 24   | 102   |
| Harp 151 | 1                         | 40   | 33   | 36   | 33   | 142   |
|          | 3                         | 41   | 28   | 32   | 21   | 122   |
|          | 5                         | 21   | 27   | 35   | 34   | 117   |
|          | 6                         | 50   | 26   | 30   | 44   | 150   |
|          | 7                         | 8    | 6    | 9    | 8    | 31    |
|          | 9                         | 4    | 17   | 32   | 10   | 63    |
| Harp 153 | 2                         | 12   | 6    | 11   | 9    | 38    |
|          | 3                         | 16   | 12   | 9    | 12   | 49    |
|          | 4                         | 6    | 5    | 7    | 3    | 21    |
|          | 5                         | 13   | 8    | 12   | 11   | 44    |
|          | 6                         | 12   | 9    | 11   | 12   | 44    |
|          | 7                         | 9    | 6    | 0    | 7    | 22    |
| Hooded 1 | 2                         | 30   | 22   | 26   | 27   | 105   |
|          | 3                         | 33   | 25   | 28   | 30   | 116   |
|          | 4                         | 37   | 32   | 38   | 34   | 141   |
|          | 5                         | 31   | 24   | 29   | 31   | 115   |
|          | 7                         | 15   | 12   | 12   | 11   | 50    |
|          | 8                         | 12   | 13   | 11   | 8    | 44    |

What is claimed is:

1. A vaccine composition, comprising:
   (a) a carrier comprising a continuous phase of a hydrophobic substance;
   (b) liposomes;
   (c) an antigen encapsulated in said liposomes, said antigen being an antigen which, when not in said vaccine composition, has a conformation other than its native conformation, with the proviso that said antigen is other than a zona pellucida-derived antigen; and,
   (d) an adjuvant.

2. The composition of claim 1, wherein the hydrophobic substance is a liquid.

3. The composition of claim 2, wherein the carrier is an oil or a water-in-oil emulsion.

4. The composition of claim 3, wherein the oil is mineral oil, a vegetable oil or a nut oil.

5. The composition of claim 3, wherein the adjuvant is alum or another compound of aluminum.

6. The composition of claim 5, wherein the adjuvant is alum.

7. The composition of claim 3, wherein the antigen is a non-native, recombinant or denatured protein, a recombinant or synthetic peptide, or a fragment thereof.

8. The composition of claim 7, wherein the antigen is a viral, bacterial, protozoal or mammalian antigen.

9. The composition of claim 8, wherein the antigen elicits an antibody that recognizes a native epitope.

10. The composition of claim 9, wherein the native epitope is a mammalian epitope.

11. The composition of claim 10, wherein the mammal is a horse, a rabbit, a deer or a cat.

12. The composition of claim 7, wherein the antigen is alcohol dehydrogenase or a hepatitis B antigen.

13. The composition of claim 3, wherein the liposomes comprise unesterified cholesterol and a phospholipid with at least one head group selected from the group consisting of phosphoglycerol, phosphoethanolamine, phosphoserine, phosphocholine and phosphoinositol.

14. The composition of claim 3 which is essentially free of lipid A.

* * * * *

UNITED STATES PATENT AND TRADEMARK OFFICE
CERTIFICATE OF CORRECTION

PATENT NO.    : 6,793,923 B2
DATED         : September 21, 2004
INVENTOR(S)   : Robert G. Brown et al.

It is certified that error appears in the above-identified patent and that said Letters Patent is hereby corrected as shown below:

Title page,
Item [75], Inventor, "William Pohajdak" should be -- Bill Pohajdak --.

Signed and Sealed this

Twenty-second Day of February, 2005

JON W. DUDAS
*Director of the United States Patent and Trademark Office*